US011779550B2

United States Patent
Andersen et al.

(10) Patent No.: US 11,779,550 B2
(45) Date of Patent: *Oct. 10, 2023

(54) BISPHENOL ETHER DERIVATIVES AND METHODS FOR USING THE SAME

(71) Applicants: THE UNIVERSITY OF BRITISH COLUMBIA, Vancouver (CA); BRITISH COLUMBIA CANCER AGENCY BRANCH, Vancouver (CA)

(72) Inventors: Raymond John Andersen, Vancouver (CA); Kunzhong Jian, Surrey (CA); Marianne Dorothy Sadar, West Vancouver (CA); Nasrin R. Mawji, Burnaby (CA); Carmen Adriana Banuelos, Richmond (CA)

(73) Assignees: The University of British Columbia, Vancouver (CA); British Columbia Cancer Agency Branch, Vancouver (CA)

( * ) Notice: Subject to any disclaimer, the term of this patent is extended or adjusted under 35 U.S.C. 154(b) by 281 days.

This patent is subject to a terminal disclaimer.

(21) Appl. No.: 17/116,070

(22) Filed: Dec. 9, 2020

(65) Prior Publication Data
US 2021/0100757 A1    Apr. 8, 2021

Related U.S. Application Data

(60) Division of application No. 16/589,853, filed on Oct. 1, 2019, now abandoned, which is a continuation of application No. 15/557,726, filed as application No. PCT/CA2016/000070 on Mar. 11, 2016, now Pat. No. 10,471,023.

(60) Provisional application No. 62/131,969, filed on Mar. 12, 2015.

(51) Int. Cl.
| | |
|---|---|
| *A61K 31/09* | (2006.01) |
| *A61K 45/06* | (2006.01) |
| *A61K 31/047* | (2006.01) |
| *C07C 43/23* | (2006.01) |
| *C07C 43/225* | (2006.01) |
| *C07C 69/18* | (2006.01) |

(52) U.S. Cl.
CPC .......... *A61K 31/09* (2013.01); *A61K 31/047* (2013.01); *A61K 45/06* (2013.01); *C07C 43/225* (2013.01); *C07C 43/23* (2013.01); *C07C 69/18* (2013.01); *A61K 2300/00* (2013.01)

(58) Field of Classification Search
CPC ...... A61K 31/09; A61K 45/06; A61K 31/047; C07C 43/23; C07C 69/18; C07C 43/225
See application file for complete search history.

(56) References Cited

U.S. PATENT DOCUMENTS

| | | | |
|---|---|---|---|
| 2,571,217 | A | 10/1951 | Davis et al. |
| 2,890,189 | A | 6/1959 | Greenlee |
| 3,162,615 | A | 12/1964 | Bremmer |
| 4,284,574 | A | 8/1981 | Bagga |
| 4,369,298 | A | 1/1983 | Kida et al. |
| 4,855,184 | A | 8/1989 | Klun et al. |
| 4,904,760 | A | 2/1990 | Gaku et al. |
| 5,043,375 | A | 8/1991 | Henning et al. |
| 5,155,196 | A | 10/1992 | Kolb et al. |
| 5,362,615 | A | 11/1994 | Hagemann et al. |
| 5,403,697 | A | 4/1995 | Doessel et al. |
| 5,753,730 | A | 5/1998 | Nagata et al. |
| 5,807,899 | A | 9/1998 | Rolf et al. |
| 5,998,674 | A | 12/1999 | Taketani et al. |
| 6,218,430 | B1 | 4/2001 | Allegretto et al. |
| 6,245,117 | B1 | 6/2001 | Nishikawa et al. |

(Continued)

FOREIGN PATENT DOCUMENTS

| | | |
|---|---|---|
| CA | 2206422 A1 | 6/1996 |
| CA | 2226469 A1 | 1/1997 |

(Continued)

OTHER PUBLICATIONS

De Santis, M et al., "Practical Guidance on the Role of Corticosteroids in the Treatment of Metastatic Castration-resistant Prostate Cancer," Urology, 2016, vol. 96, pp. 156-164.

(Continued)

*Primary Examiner* — Erich A Leeser
(74) *Attorney, Agent, or Firm* — COOLEY LLP

(57) ABSTRACT

Compounds having a structure of Formula I:

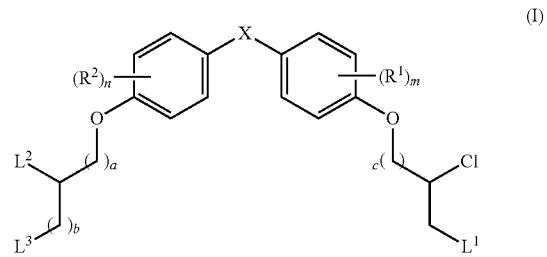

or a pharmaceutically acceptable salt, tautomer or stereoisomer thereof, wherein $R^1$, $R^2$, $L^1$, $L^2$, $L^3$, X, a, b, c, n, and m are as defined herein, are provided. Uses of such compounds for modulating androgen receptor activity and uses as therapeutics as well as methods for treatment of subjects in need thereof, including prostate cancer are also provided.

10 Claims, 9 Drawing Sheets

(56) References Cited

U.S. PATENT DOCUMENTS

| | | | |
|---|---|---|---|
| 7,183,323 B2 | 2/2007 | Chinn et al. | |
| 7,273,867 B2 | 9/2007 | Dorsch et al. | |
| 7,595,345 B2 | 9/2009 | Bunel et al. | |
| 7,666,868 B2 | 2/2010 | Maier et al. | |
| 7,674,795 B2 | 3/2010 | Mailliet et al. | |
| 8,048,888 B2 | 11/2011 | Wosikowski-Buters et al. | |
| 8,445,507 B2 | 5/2013 | Jung | |
| 8,455,477 B2 | 6/2013 | Katz | |
| 8,686,050 B2 | 4/2014 | Sadar et al. | |
| 9,173,939 B2 | 11/2015 | Andersen et al. | |
| 9,365,510 B2 | 6/2016 | Andersen et al. | |
| 9,375,496 B2 | 6/2016 | Andersen et al. | |
| 9,388,112 B2 | 7/2016 | Sadar et al. | |
| 9,862,667 B2 | 1/2018 | Sadar et al. | |
| 10,471,023 B2 * | 11/2019 | Andersen | A61K 45/06 |
| 10,654,811 B2 | 5/2020 | Andersen et al. | |
| 11,059,795 B2 | 7/2021 | Zhou et al. | |
| 11,142,508 B2 | 10/2021 | Andersen et al. | |
| 11,242,324 B2 | 2/2022 | Zhou et al. | |
| 11,345,670 B2 | 5/2022 | Andersen et al. | |
| 11,358,938 B2 | 6/2022 | Zhou et al. | |
| 11,485,713 B2 | 11/2022 | Zhou et al. | |
| 11,518,747 B2 | 12/2022 | Zhou et al. | |
| 2003/0092724 A1 | 5/2003 | Kao et al. | |
| 2003/0105268 A1 | 6/2003 | Boriack et al. | |
| 2004/0049004 A1 | 3/2004 | Boriack et al. | |
| 2004/0243316 A1 | 12/2004 | Weinmann et al. | |
| 2008/0153837 A1 | 6/2008 | Mailliet et al. | |
| 2008/0193380 A1 | 8/2008 | Dalton et al. | |
| 2008/0255395 A1 | 10/2008 | Dai et al. | |
| 2009/0105349 A1 | 4/2009 | Barvian et al. | |
| 2009/0246158 A1 | 10/2009 | Rudolph et al. | |
| 2011/0230556 A1 | 9/2011 | Sadar et al. | |
| 2013/0045204 A1 | 2/2013 | Sadar et al. | |
| 2013/0109758 A1 | 5/2013 | Sadar et al. | |
| 2013/0131167 A1 | 5/2013 | Sadar et al. | |
| 2013/0245129 A1 | 9/2013 | Sadar et al. | |
| 2013/0336962 A1 | 12/2013 | Andersen et al. | |
| 2014/0248263 A1 | 9/2014 | Andersen et al. | |
| 2014/0335080 A1 | 11/2014 | Andersen et al. | |
| 2015/0010469 A1 | 1/2015 | Andersen et al. | |
| 2015/0125389 A1 | 5/2015 | Andersen et al. | |
| 2015/0210681 A1 | 7/2015 | Bourque et al. | |
| 2016/0068466 A1 | 3/2016 | Andersen et al. | |
| 2016/0367707 A1 | 12/2016 | Andersen et al. | |
| 2017/0056336 A1 | 3/2017 | Sadar et al. | |
| 2017/0081192 A1 | 3/2017 | Schwab et al. | |
| 2017/0121261 A1 | 5/2017 | Sadar et al. | |
| 2017/0298033 A1 | 10/2017 | Andersen et al. | |
| 2017/0368036 A1 | 12/2017 | Hattersley et al. | |
| 2018/0064657 A1 | 3/2018 | Andersen et al. | |
| 2018/0235925 A1 | 8/2018 | Andersen et al. | |
| 2018/0327368 A1 | 11/2018 | Andersen et al. | |
| 2019/0022093 A1 | 1/2019 | Wipf et al. | |
| 2019/0202800 A1 | 7/2019 | Freeman et al. | |
| 2020/0123117 A1 | 4/2020 | Zhou et al. | |
| 2020/0247763 A1 | 8/2020 | Zhou et al. | |
| 2020/0281949 A1 | 9/2020 | Warner et al. | |
| 2020/0325106 A1 | 10/2020 | Andersen et al. | |
| 2021/0198213 A1 | 7/2021 | Zhou et al. | |
| 2021/0323931 A1 | 10/2021 | Zhou et al. | |
| 2021/0332016 A1 | 10/2021 | Zhou et al. | |
| 2021/0387957 A1 | 12/2021 | Andersen et al. | |
| 2022/0073472 A1 | 3/2022 | Zhou et al. | |
| 2022/0105093 A1 | 4/2022 | Virsik et al. | |
| 2022/0202780 A1 | 6/2022 | Virsik et al. | |
| 2023/0078913 A1 | 3/2023 | Zhou et al. | |

FOREIGN PATENT DOCUMENTS

| | | |
|---|---|---|
| CA | 2339775 A1 | 3/2000 |
| CA | 2606262 A1 | 11/2006 |
| CA | 2728219 A1 | 1/2010 |
| CA | 2786319 A1 | 7/2011 |
| CN | 102083780 A | 6/2011 |
| CN | 103342892 A | 10/2013 |
| EA | 009199 B1 | 12/2007 |
| EP | 0056175 A1 | 7/1982 |
| EP | 0293768 A1 | 12/1988 |
| EP | 0515128 A1 | 11/1992 |
| FR | 1389005 | 2/1965 |
| JP | B-S45-008432 | 3/1970 |
| JP | S56-5472 A | 1/1981 |
| JP | 63-196675 | 8/1988 |
| JP | S63-317539 A | 12/1988 |
| JP | H01-503541 | 11/1989 |
| JP | H02-4815 | 1/1990 |
| JP | 6-049473 A2 | 2/1994 |
| JP | 7-117349 A | 5/1995 |
| JP | 09-176240 A | 7/1997 |
| JP | H10133427 A | 5/1998 |
| JP | A-H10-316803 | 12/1998 |
| JP | 11-166087 A2 | 6/1999 |
| JP | 2000-072705 A2 | 3/2000 |
| JP | 2001-511170 A | 8/2001 |
| JP | 2005-325301 A | 11/2005 |
| JP | 2006-208607 A | 8/2006 |
| JP | 2006-265351 A2 | 10/2006 |
| JP | 2007-513089 A | 5/2007 |
| JP | 2007-290980 | 11/2007 |
| KR | 10-2011-0044216 A | 4/2011 |
| PL | 141793 B1 | 8/1987 |
| RU | 2454394 C2 | 6/2012 |
| SU | 638596 | 12/1978 |
| SU | 929630 | 5/1982 |
| WO | WO 1988/009782 A1 | 12/1988 |
| WO | WO 1996/16646 A1 | 6/1996 |
| WO | WO 1998/034930 A1 | 8/1998 |
| WO | WO 2000/001813 A2 | 1/2000 |
| WO | WO 2000/010958 A1 | 3/2000 |
| WO | WO 2001/088013 A2 | 11/2001 |
| WO | WO 2002/005813 A2 | 1/2002 |
| WO | WO 2003/004481 A1 | 1/2003 |
| WO | WO 2005/042464 A1 | 5/2005 |
| WO | WO 2005/077967 A1 | 8/2005 |
| WO | WO-2007079078 A1 | 7/2007 |
| WO | WO 2008/101806 A2 | 8/2008 |
| WO | WO 2010/000066 A1 | 1/2010 |
| WO | WO 2011/082487 A1 | 7/2011 |
| WO | WO 2011/082488 A1 | 7/2011 |
| WO | WO-2011103202 A2 | 8/2011 |
| WO | WO 2012/139039 A2 | 10/2012 |
| WO | WO 2012/145328 A1 | 10/2012 |
| WO | WO 2012/145330 A1 | 10/2012 |
| WO | WO 2013/028572 A1 | 2/2013 |
| WO | WO 2013/028791 A1 | 2/2013 |
| WO | WO 2014/011220 A2 | 1/2014 |
| WO | WO 2014/179867 A1 | 11/2014 |
| WO | WO 2015/031984 A1 | 3/2015 |
| WO | WO 2016/058080 A1 | 4/2016 |
| WO | WO 2016/058082 A1 | 4/2016 |
| WO | WO 2016/112455 A1 | 7/2016 |
| WO | WO 2016/141458 A1 | 9/2016 |
| WO | WO 2017/177307 A1 | 10/2017 |
| WO | WO 2017/210771 A1 | 12/2017 |
| WO | WO 2018/045450 A1 | 3/2018 |
| WO | WO 2018/157232 A1 | 9/2018 |
| WO | WO 2019/226991 A1 | 11/2019 |
| WO | WO 2020/081999 A1 | 4/2020 |
| WO | WO 2020/198710 A1 | 10/2020 |
| WO | WO 2020/198711 A1 | 10/2020 |
| WO | WO 2020/198712 A1 | 10/2020 |

OTHER PUBLICATIONS

Mathur, A et al., "Subverting ER-Stress towards Apoptosis by Nelfinavir and Curcumin Coexposure Augments Docetaxel Efficacy in Castration Resistant Prostate Cancer Cells," PLoS ONE (2014) 9(8): e103109, 14 pages.

McClurg, UL et al., "The novel anti-androgen candidate galeterone targets deubiquitinating enzymes, USP12 and USP46, to control prostate cancer growth and survival," Oncotarget, 2018, vol. 9, No. 38, pp. 24992-25007.

(56) References Cited

OTHER PUBLICATIONS

Qin et al., "Discovery of QCA570 as an Exceptionally Potent and Efficacious Proteolysis Targeting Chimera (PROTAC) Degrader of the Bromodomain and Extra-Terminal (BET) Proteins Capable of Inducing Complete and Durable Tumor Regression," J Med Chem. 2018. vol. 61(15), pp. 6665-6704.
Raina et al., "PROTAC-induced BET protein degradation as a therapy for castration-resistant prostate cancer," PNAS, Jun. 28, 2016, vol. 113, No. 26, pp. 7124-7129.
Zurth, "Drug-Drug Interaction Potential of Darolutamide: In Vitro and Clinical Studies," European Journal of Drug Metabolism and Pharmacokinetics (2019) 44:747-759.
Extended European Search Report in Application No. 21212648.6 dated Feb. 21, 2022, 8 pages.
International Search Report and Written Opinion for International Application No. PCT/US2020/025545 dated Jul. 9, 2020, 11 pages.
International Search Report and Written Opinion for International Application No. PCT/US2020/025542 dated Aug. 14, 2020, 10 pages.
International Search Report and Written Opinion for International Application No. PCT/US2020/025539 dated Aug. 18, 2020, 11 pages.
International Search Report and Written Opinion for International Application No. PCT/US2021/027771 dated Jul. 9, 2021, 8 pages.
International Search Report and Written Opinion for International Application No. PCT/US2021/050644 dated Feb. 3, 2022, 12 pages.
Alabi, A. et al., "Quick and simple sample treatment for multiresidue analysis of bisphenols, bisphenol diglycidyl ethers and their derivatives in canned food prior to liquid chromatography and fluorescence detection," J. of Chromatography A, 2014, 1336, 23-33.
Alvarez, C. et al., "Conformational and Experimental Studies on the Dipole Moments of Models of Comblike Polymers", Macromolecules, 30(20): 6369-6375 (1997).
Anderson, R. et al., "Regression of Castrate-Recurrent Prostate Cancer by a Small-Molecule Inhibitor of the Amino-Terminus Domain of the Androgen Receptor", Cancer Cell, 17:535-546 (2010).
Anton, R. et al., Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A diglycidyl ether, BADGE), Ref. No. 13510 and 39700 (EFSA-Q-2003-178), The EFSA Journal, 86:1-40 (2004).
Antonarakis et al., "Androgen receptor variant-driven prostate cancer: clinical implications and therapeutic targeting," Prostate Cancer and Prostatic Diseases (2016), 1-11.
Antonarakis et al., "Targeting the N-Terminal Domain of the Androgen Receptor: A New Approach for the Treatment of Advanced Prostate Cancer," The Oncologist 2016;21:1-9.
Auzou et al., European Journal of Medicinal Chemistry, 9(5):548-554 (1974) (with English Abstract).
Balbay, M.D. et al., "Highly Metastatic Human Prostate Cancer Growing within the Prostate of Athymic Mice Overexpresses Vascular Endothelial Growth Factor", Clinical Cancer Research, 5:783-789 (1999).
Banker (ed.) et al., Modern Pharmaceutics, Third Edition, Revised and Expanded, Marcel Dekker, Inc., 1997, pp. 451 and 596.
Banuelos et al., "Sintokamide A is a novel antagonist of androgen receptor that uniquely binds activation function-1 in its amino-terminal domain," The Journal of Biological Chemistry, vol. 291, No. 42, pp. 22231-22243, Oct. 14, 2016.
Bao, B. et al., "Androgen signaling is required for the vitamin D-mediated growth inhibition in human prostate cancer cells", Oncogene, 23:3350-3360 (2004).
Berge, S.M. et al., "Pharmaceutical Salts", Pharmaceutical Sciences, 66(1):1-19 (1977).
Berger, U. et al., "Identification of Derivatives of Bisphenol A Diglycidyl Ether and Novolac Glycidyl Ether in Can Coatings by Liquid Chromatography/Ion Trap Mass Spectrometry," Journal of AOAC International, Food Chemical Contaminants, 83(6):1367-1376 (2000).
Biles, J.E. et al., "Determination of the Diglycidyl Ether of Bisphenol A and its Derivatives in Canned Foods", J. Agric. Food Chem., 47:1965-1969 (1999).
Bisson, W.H. et al., "Discovery of antiandrogen activity of nonsteroidal scaffolds of marketed drugs", PNAS, 104(29):11927-11932 (2007).
Blaszczyk, N. et al., "Osteoblast-Derived factors Induce Androgen-Independent Proliferation and Expression of Prostate-Specific Antigen in Human Prostate Cancer Cells", Clin. Cancer Res., 10:1860-1869 (2004).
Bodei, et al., "Radionuclide Therapy with Iodine-125 and Other Auger-Electron-Emitting Radionuclides: Experimental Models and Clinical Applications." Cancer Biother. & Radiopharm. (2003); 18(6): 861-877.
Bohler, Paul et al., "Identification of Migrants from Coatings of Food Cans and Tubes: Reaction Products of Bisphenol-A-Diglycidyl Ether (BADGE) with Phenols and Solvents", Mitt. Gebiete Lebensm. Hyg., 89:529-547 (1998).
Brand et al., "EPI-001 is a selective peroxisome proliferator-activated receptor-gamma modulator with inhibitory effects on androgen receptor expression and activity in prostate cancer." Oncotarget (2015); 6(6): 3811-3824.
Brzozowski, Z. et al., "Precursors for bisphenolic resins", CAPLUS Database Accession No. 1990:36690, Document No. 112:33690, (1987), 1 page (Abstract).
Bruckheimer, E.M. et al., "Apoptosis in prostate carcinogenesis a growth regulator and a therapeutic target", Cell Tissue Res, 301:153-162 (2000).
Cascini, et al., "$^{124}$Iodine: A Longer-Life Positron Emitter Isotope—New Opportunities in Molecular Imaging." Hindawi Publishing Corp.Biomed. Res. Int. (2014); vol. 2014, Article ID 672094, 7 pages.
Chang, C. et al., "Development of Peptide Antagonists for the Androgen Receptor Using Combinatorial Peptide Phage Display", Molecular Endocrinology, 19(10):2478-2490 (2005).
Choi, K. M. et al., "New Families of Photocurable Oligomeric Fluoromonomers for Use in Dental Composites", Chemistry of Materials, 8(12):2704-2707 (1996).
Clinton, G.M. et al., "Estrogen action in human ovarian cancer", Critical Reviews in Oncology/Hematology, 25:1-9 (1997).
Crivello, J. V. et al., "Synthesis and photopolymerization of multifunctional propenyl ether monomers," Database CAPLUS [online], Chemical Abstracts Service, Columbus, Ohio, US, XP002729292, retrieved from STN CA Caesar Accession No. 1994-606067 (1994), 3 pages.
Crivello, J. V. et al., "Synthesis and photopolymerization of multifunctional propenyl ether monomers", Journal of Macromolecular Science, Pure and Applied Chemistry,A31(9):1105-1119 (1994).
Cook, W. D., "Fracture and Structure of Highly Crosslinked Polymer Composites", Journal of Applied Polymer Science, 42:1259-1269 (1991).
Culig, Zoran et al., "Androgen Receptor Activation in Prostatic Tumor Cell Lines by Insulin-like Growth Factor-I, Keratinocyte Growth Factor, and Epidermal Growth Factor", Cancer Research, 54:5474-5478 (1994).
Danquah, M. et al., "Micellar Delivery of Bicalutamide and Embelin for Treating Prostate Cancer", Pharmaceutical Research, 26:2081-2092 (2009).
Das, Debasish et al., "Sulfonic acid functionalized mesoporous MCM-41 silica as a convenient catalyst for Bisphenol-A synthesis", Chemical Communications, pp. 2178-2179 (2001).
De Mol et al., "EPI-001, a compound active against castration-resistant prostate cancer, targets transactivation unit 5 of the androgen receptor," ACS Chem. Biol., 2016, 11, 9, 2499-2505.
Dehm, S. et al., "Ligand-independent Androgen Receptor Activity is Activation Function-2-independent and Resistant to Antiandrogens in Androgen Refractory Prostate Cancer Cells", The Journal of Biological Chemistry, 281(38):27882-27893 (2006).

(56) References Cited

OTHER PUBLICATIONS

Dehm, S. et al., "Splicing of a Novel Androgen Receptor Exon Generates a Constitutively Active Androgen Receptor that Mediates Prostate Cancer Therapy Resistance", Cancer Research, 68:5469-5477 (2008).
Edmondson, R.J., et al., "The human ovarian surface epithelium is an androgen responsive tissue", British Journal of Cancer, 86:879-885 (2002).
Estebanez-Perpiña, E. et al., "A surface on the androgen receptor that allosterically regulates coactivator binding," PNAS, 104(41):16074-16079 (2007).
Estebanez-Perpiña, E. et al., "The Molecular Mechanisms of Coactivator Utilization in Ligand-dependent Transactivation by the Androgen Receptor," The Journal of Biological Chemistry, 280(9):8060-8068 (2005).
Fehlberg S. et al., "Bisphenol A diglycidyl ether induces apoptosis in tumor cells independently of peroxisome proliferator-activated receptor-γ, in caspase-dependent and -independent manners," Biochem. J., 362:573-578 (2002).
Gallart-Ayala, H. et al., "The analysis of bisphenol A-diglycidyl ether (BADGE), bisphenol F-diglycidyl ether (BFDGE) and their derivatives in canned food and beverages by LC-MS/MS", Thermo Fisher Scientific Inc., 4 pages (2011).
Garuti, L., et al., "Irreversible Protein Kinase Inhibitors", Current Medicinal Chemistry, 18:2981-2994 (2011).
Garcia et al., "Determination of compounds from epoxy resins in food simulants by HPLC-fluorescence." Chromatographia, 58(5-6): 337-342 (2003).
Gleave, Martin et al., "Acceleration of Human Prostate Cancer Growth in Vivo by Factors Produced by Prostate and Bone Fibroblasts", Cancer Research, 51:3753-3761 (1991).
Gregory, Christopher et al., "Epidermal Growth Factor Increases Coactivation of the Androgen Receptor in Recurrent Prostate Cancer", The Journal of Biological Chemistry, 279(8):7119-7130 (2004).
Guinan, P.D. et al., "Impotence Therapy and Cancer of the Prostate", The American Journal of Surgery, 131:599-600 (1976).
Guo, Zhiyong et al., "A Novel Androgen Receptor Splice Variant Is Up-regulated during Prostate Cancer Progression and Promotes Androgen Depletion—Resistant Growth", Cancer Research, 69:2305-13 (2009).
Haggstrom, Stina et al., "Testosterone Induces Vascular Endothelial Growth Factor Synthesis in the Ventral Prostate in Castrated Rats", The Journal of Urology, 161:1620-1625 (1999).
Harper et al., "Expression of Androgen Receptor and Growth Factors in Premalignant Lesions of the Prostate", Journal of Pathology, 186:169-177 (1998).
He, B. et al., "Activation Function 2 in the Human Androgen Receptor Ligand Binding Domain Mediates Interdomain Communication with the $NH_2$-terminal Domain", The Journal of Biological Chemistry, 274(52):37219-37225 (1999).
He, B. et al., "Structural Basis for Androgen Receptor Interdomain and Coactivator Interactions Suggests a Transition in Nuclear Receptor Activation Function Dominance", Molecular Cell, 16:425-438 (2004).
Henke, H., "Selektive präparative gelchromatographische Trennung niedermolekularer Verbindungen an Sephadex LH-20", Journal of Chromatography, 254: 296-308 (1983).
Heinlein, Cynthia A., et al., "Androgen Receptor in Prostate Cancer", Endocrine Reviews, 25(2):276-308 (2004).
Helzlsouer, Kathy J., et al., "Serum Gonadotropins and Steroid Hormones and the Development of Ovarian Cancer", JAMA, 274(24):1926-1930 (1995).
Horoszewicz, J.S. et al., "LNCaP Model of Human Prostatic Carcinoma", Cancer Research, 43:1809-1818 (1983).
Hu, R. et al., "Ligand-Independent Androgen Receptor Variants Derived from Splicing of Cryptic Exons Signify Hormone-Refractory Prostate Cancer", Cancer Research, 69:16-22 (2009).
Huber, P.R. et al., "Prostate Specific Antigen. Experimental and Clinical Observations", Scand. J. Urol Nephrol., 104:33-39 (1987).
Hur, E. et al., "Recognition and Accommodation at the Androgen Receptor Coactivator Binding Interface", PLoS Biology, 2(9)(e274):1303-1312 (2004).
Imamura et al., "An imaging agent to detect androgen receptor and its active splice variants in prostate cancer," JCI Insight. 2016;1(11):e87850 15 pages.
Imamura et al., "Androgen receptor targeted therapies in castration-resistant prostate cancer: Bench to clinic," International Journal of Urology (2016), 23(8):654-65.
Isaacs, J.T., et al., "New Biochemical Methods to Determine Androgen Sensitivity of Prostatic Cancer: The Relative Enzymatic Index (REI)", Prostate Cancer and Hormone Receptors, pp. 133-144 (1979).
Isaacs, J.T., "Antagonistic Effect of Androgen on Prostatic Cell Death", The Prostate, 5:545-557 (1984).
Jackson, J. A. et al., "Prostatic Complications of Testosterone Replacement Therapy", Arch Intern Med., 149:2365-2366 (1989).
Japanese Patent Application No. 2016-512175, Notice of Reasons for Rejection dated Jun. 21, 2016 (and English translation), 12 pages.
Jenster, G. et al., "Domains of the Human Androgen Receptor Involved in Steroid Binding, Transcriptional Activation, and Subcellular Localization", Molecular Endocrinology, 5:1396-1404 (1991).
Jenster, G., et al. "Identification of two transcription activation units in the N-terminal domain of the human androgen receptor." Journal of Biological Chemistry (1995); 270.13: 7341-7346.
Jia, L. et al., "Androgen Receptor Signaling: Mechanism of Interleukin-6 Inhibition", Cancer Research, 64:2619-2626 (2004).
Jia, L. et al., "Androgen Receptor-Dependent PSA Expression in Androgen-Independent Prostate Cancer Cells Does Not Involve Androgen Receptor Occupancy of the PSA Locus", Cancer Research, 65:8003-8008 (2005).
Kaighn, M.E. et al., "Prostate Carcinoma: Tissue Culture Cell Lines", National Cancer Institute Monograph No. 49, pp. 17-21 (1978).
Kato, M. et al., "Cotargeting androgen receptor splice variants and mTOR signaling pathway for the treatment of castration-resistant prostate cancer," Clin Cancer Res, Jun. 2016, vol. 22, pp. 2744-2754.
Kemppainen, J. A. et al., "Distinguishing Androgen Receptor Agonists and Antagonists: Distinct Mechanisms of Activation by Medroxyprogesterone Acetate and Dihydrotestosterone", Mol. Endocrinol., 13:440-454 (1999).
Kim, D. et al., "Androgen Receptor Expression and Cellular Proliferation During Transition from Androgen-Dependent to Recurrent Growth after Castration in the CWR22 Prostate Cancer Xenograft", American Journal of Pathology, 160(1):219-226 (2002).
Kolbel, M. et al., "Design of Liquid Crystalline Block Molecules with Nonconventional Mesophase Morphologies: Calamitic Bolaamphiphiles with Lateral Alkyl Chains", J. Am. Chem. Soc., 123:6809-6818 (2001).
Kumar, S. et al., "Synthesis of new crown analogs derived from bisphenol," Indian Journal Chemistry, 36B:656-661 (1997).
L'Heureux, A. et al., "Aminodifluorosulfinium Salts: Selective Fluorination Reagents with Enhanced Thermal Stability and Ease of Handling", J. Org. Chem, 75:3401-3411 (2010).
Langley, E. et al., "Evidence for an Anti-parallel Orientation of the Ligand-activated Human Androgen Receptor Dimer", The Journal of Biological Chemistry, 270(50):29983-29990 (1995).
Lannoye, G.S. et al., "N-Fluoroalkylated and N-alkylated analogs of the dopaminergic D-2 receptor antagonist raclopride", J. Med. Chem., 33(9):2430-2437 (1990).
Leepipatpiboon, N. et al., "Simultaneous determination of bisphenol-A-diglycidyl ether, bisphenol-F-diglycidyl ether, and their derivatives in oil-in-water and aqueous-based canned foods by high-performance liquid chromatography with fluorescence detection." Journal of Chromatography A (2005); 1073.1: 331-339.
Levoin et al., "Determination of the binding mode and interacting amino-acids for dibasic H3 receptor antagonists", Bioorganic & Medicinal Chemistry, 21 (2013) 4526-4529 and Levoin et al., "Supporting Information—Determination of the binding mode and interacting amino-acids for dibasic H3 receptor agonists", Bioorganic & Medicinal Chemistry, vol. 21, Jan. 2013, pp. S1-S3.

(56) References Cited

OTHER PUBLICATIONS

Loren, J.C. et al., "Synthesis of achiral and racemic catenanes based on terpyridine and a directionalized terpyridine mimic, pyridyl-phenanthroline", Org. Biomol. Chem., 3(17):3105-3116 (2005).
Louie, M.C. et al., "Androgen-induced recruitment of RNA polymerase II to a nuclear receptor-p160 coactivator complex", PNAS, 100(5):2226-2230 (2003).
Makary, P., "Principles of salt formation." UK Journal of Pharmaceutical and Biosciences (2014); 2(4): 01-04.
Marriott et al., "Pharmaceutical Compounding and Dispensing," Second Edition, Pharmaceutical Press, 305 pages (2005).
Martin, S.J. et al., "A new precursor for the radiosynthesis of [$^{18}$F]FLT", Nuclear Medicine and Biology, 29:263-273 (2002).
Martin, S.K. et al., "N-terminal targeting of androgen receptor variant enhances response of castration resistant prostate cancer to taxane chemotherapy," Molecular Oncology, 2015, vol. 9, pp. 628-639.
Masiello, D. et al., "Bicalutamide Functions as an Androgen Receptor Antagonist by Assembly of a Transcriptionally Inactive Receptor", The Journal of Biological Chemistry, 277(29):26321-26326 (2002).
Mawji et al., "Preparation of ester derivatives of bisphenol-related compounds as androgen receptor modulators", CAPLUS Database Accession No. 2014:1909735, Document No. 161:737220, Entered on Jan. 6, 2015, 7 pages (Abstract).
Melnyk, O. et al., "Neutralizing Anti-Vascular Endothelial Growth Factor Antibody Inhibits Further Growth of Established Prostate Cancer and Metastases in a Pre-Clinical Model", The Journal of Urology, 161:960-963 (1999).
Miller, J.I. et al., "The Clinical Usefulness of Serum Prostate Specific Antigen After Hormonal Therapy of Metastatic Prostate Cancer", The Journal of Urology, 147:956-961 (1992).
Mitsiades, C.S. et al., "Molecular biology and cellular physiology of refractoriness to androgen ablation therapy in advanced prostate cancer", Expert Opin. Investig. Drugs, 10(6):1099-1115 (2001).
Lima, Lidia M., and Barreiro, Eliezer J. "Bioisosterism: a useful strategy for molecular modification and drug design." Current Medicinal Chemistry (2005); 12.1: 23-49.
Myung, J-K et al., "An androgen receptor N-terminal domain antagonist for treating prostate cancer", The Journal of Clinical Investigation, 123(7):2948-2960 (2013).
Nakazawa, H. et al., "In vitro assay of hydrolysis and chlorohydroxy derivatives of bisphenol A diglycidyl ether for estrogenic activity", Food and Chemical Toxicology, 40:1827-1832 (2002).
Nazareth, L.V. et al., "Activation of the Human Androgen Receptor through a Protein Kinase A Signaling Pathway", The Journal of Biological Chemistry, 271(33):19900-19907 (1996).
Nedolya, N. A. et al., Zhurnal Organicheskoi Khimii, 30(8):1163-1166 (1994) (non English document).
Nishikawa et al., "Epichlorohydrin derivative-based modifier of cellulose fibers and modification method of cellulose fibers," Accession No. 2000:98153 CAPLUS (2009).
Noble, R. L., "The development of prostatic adenocarcinoma in Nb Rats following prolonged sex hormone administration", Cancer Research, 37:1929-1933 (1977).
Noble, R. L., "Sex steroids as a cause of adenocarcinoma of the dorsal prostate in Nb Rats, and their influence on the growth of transplants", Oncology, 34:138-141 (1977).
Ogawa, Y. et al., "Estrogenic activities of chemicals related to food contact plastics and rubbers tested by the yeast two-hybrid assay," Food Additives and Contaminants, 23:4, 422-430 (2006).
Paris, F. et al., "Phenylphenols, biphenols, bisphenol-A and 4-tert-octyphenol exhibit α and β estrogen activities and antiandrogen activity in reporter cell lines," Molecular and Cellular Endocrinology, 193:43-49 (2002).
Patani and LaVoie, "Bioisosterism: A Rational Approach in Drug Design", Chem. Rev., 96: 3147-3176 (1996).
Penczek, P. et al., "Synthesis and cyclotrimerization of dipropargyl derivatives of diepoxides," Database CAPLUS [Online] Chemical Abstracts Service, Columbus, Ohio, retrieved from STN CA Caesar Accession No. 1995:741510 (1995), 2 pages.
Penczek, P. et al., "Synthesis and cyclotrimerization of dipropargyl derivatives of diepoxides," Polimery, (Warsaw), 40(5):274-277 (1995).
Petersen, H. et al., "Determination of bisphenol A diglycidyl ether (BADGE) and its derivatives in food: identification and quantification by internal Standard", Eur. Food Res. Technol., 216:355-364 (2003).
Poouthree, K. et al., "Comparison of resolution in microemulsion EKC and MEKC employing suppressed electroosmosis: Application to bisphenol-A-diglycidyl ether and its derivatives", Electrophoresis, 28(20):3705-3711 (2007).
Poustka, J. et al., "Determination and occurrence of bisphenol A, bisphenol A diglycidyl ether, and bisphenol F diglycidyl ether, including their derivatives, in canned foodstuffs' from the Czech retail market," Czech J. Food Sci., 25(4):221-229 (2006).
Poustková et al., "Stability of bisphenol A diglycidyl ether and bisphenol F diglycidyl ether in water-based food simulants." European Food Research and Technology, 219(5): 534-539 (2004).
PubChem Compound Summary for CID 15305867, '4-Acetyl-4'-ethylbiphenyl', U.S. National Library of Medicine, Feb. 9, 2007, pp. 1-17; retrieved from https://pubchem.ncbi.nlm.nih.gov/compound/15305867.
PubChem Compound Summary for CID 18533308, '2-[4-[[4-(Aminomethoxy)phenyl]methyl]-2-methylphenoxy]acetic acid', U.S. National Library of Medicine, Dec. 4, 2007, pp. 1-15 retrieved from https://pubchem.ncbi.nlm.nih.gov/compound/18533308.
Quayle, S. et al., "Androgen receptor decoy molecules block the growth of prostate cancer", PNAS, 104(4):1331-1336 (2007).
Rao, B.R. et al., "Endocrine Factors in Common Epithelial Ovarian Cancer", Endocrine Reviews, 12(1):14-26 (1991).
Reader, C. E. L., "Epoxy Resin Derivatives for Stoving Systems", Surface Coatings Australia, 25(10):6-9 (1988).
Reid, J. et al., "Conformational Analysis of the Androgen Receptor Amino-terminal Domain Involved in Transactivation," The Journal of Biological Chemistry, 277:20079-20086 (2002).
Risch, H.A., "Hormonal Etiology of Epithelial Ovarian Cancer, With a Hypothesis Concerning the Role of Androgens and Progesterone", Journal of the National Cancer Institute, 90(23):1774-1786 (1998).
Riu, A. et al., "Characterization of Novel Ligands of ERα, Erβ, and PPARγ: The Case of Halogenated Bisphenol A and Their Conjugated Metabolites", Toxicology Sciences, 122(2): 372-382 (2011).
Roberts, J. T. et al., "Adenocarcinoma of Prostate in 40-Year-Old Body-Builder", Lancet, 2:742 (1986).
Roberts et al., "Emerging drugs for hepatocellular carcinoma," Expert Opin Emerg Drugs, 11(3):469-487 (2006).
Rokicki, G. et al., "Reactions of 4-chloromethyl-1,3-dioxolan-2-one with phenols as a new route to polyols and cyclic carbonates", Journal f. prakt. Chemie., 327:718-722 (1985).
Ross, R.K. et al., "Androgen Metabolism and Prostate Cancer: Establishing a Model of Genetic Susceptibility", European Urology, 35:355-361 (1999).
Roulin et al., "Targeting renal cell carcinoma with NVP-BEZ235, a dual PI3K/mTOR inhibitor, in combination with sorafenib," Mol Cancer, 10:90 (2011), 12 pages.
Rusu, E. et al.: "Photosensitive compounds with chloromethyl groups", Revue Roumaine de Chimie, 45(5):451-456 (2000).
Sadar, M., "Androgen-independent Induction of Prostate-specific Antigen Gene Expression via Cross-talk between the Androgen Receptor and Protein Kinase A signal Transduction Pathways," The Journal of Biological Chemistry, 274(12):7777-7783 (1999).
Sadar, M. et al., "Prostate cancer: molecular biology of early progression to androgen independence", Endocrine-Related Cancer, 6:487-502 (1999).
Sadar, M.D. et al., "Characterization of a New in Vivo Hollow Fiber Model for the Study of Progression of Prostate Cancer to Androgen Independence", Molecular Cancer Therapeutics, 1:629-637 (2002).
Sato, N. et al., "Intermittent Androgen Suppression Delays Progression to Androgen-independent Regulation of Prostate-specific Antigen Gene in the LNCaP Prostate Tumour Model", J. Steroid Biochem. Mol. Biol., 58:139-146 (1996).

(56) References Cited

OTHER PUBLICATIONS

Sato, N. et al., "A Metastatic and Androgen-sensitive Human Prostate Cancer Model Using Intraprostatic Inoculation of LNCaP Cells in SCID Mice", Cancer Research, 57:1584-1589 (1997).
Satoh, K. et al., "Study on Anti-Androgenic Effects of Bisphenol a Diglycidyl Ether (BADGE), Bisphenol F Diglycidyl Ether (BFDGE) and Their Derivatives Using Cells Stably Transfected with Human Androgen Receptor, AR-EcoScreen", Food and Chemical Toxicology, 42:983-993 (2004).
Schaefer, A. et al., "Migration from can coatings: Part 3. Synthesis, identification and quantification of migrating epoxy-based substances below 1000 Da", Food Additives and Contaminants, 21(4):390-405 (2004).
Schellhammer, "An evaluation of bicalutamide in the treatment of prostate cancer." Expert Opinion on Pharmacotherapy, 3(9): 1313-1328 (2002).
Sharp et al., "Targeting Androgen Receptor Aberrations in Castration-Resistant Prostate Cancer," Clin Cancer Res., Sep. 1, 2016;22(17):4280-4282.
Silverman, R. B., The Organic Chemistry of Drug Design and Drug Action, Academic Press, Inc., Harcourt Brace Jovanovich, pp. 15-20, 9 pages (1992).
Snoek, R. et al., "Induction of Cell-free, In Vitro Transcription by Recombinant Androgen Receptor Peptides", J. Steroid Biochem. Mol. Biol., 59:243-250 (1996).
Stanciuc et al., "Reaction of Pyrylium Salts with Nucleophiles. 23: Triarylethene Derivatives Containing an Oxyalkyleneamino or Oxyalkylene-N-pyridinium Side Chain", Journal of Pharmaceutical Sciences, vol. 82, No. 9, Sep. 1993, pp. 927-933.
Still, W. C. et al., "Rapid Chromatographic Technique for Preparative Separations with Moderate Resolution", J. Org. Chem., 43(14):2923-2925 (1978).
STN Structure Search, dated Oct. 30, 2014 citing PL 135932, 3 pages.
Strub and McKim, "Dimethyl Sulfoxide USP, PhEur in Approved Pharmaceutical Products and Medical Devices", PharmaTech.com, 6 pages (2008). http://www.pharmtech.com/print/224268 ?page=full&rel=canonical.
Sun, S. et al., "Castration resistance in human prostate cancer is conferred by a frequently occurring androgen receptor splice variant", The Journal of Clinical Investigation, 120(8):2715-30 (2010).
Tanji, N. et al., "Growth Factors: Roles in Andrology", Archives of Andrology, 47:1-7 (2001).
Taplin, M.E. et al., "Selection for Androgen Receptor Mutations in Prostate cancers Treated with Androgen Antagonist", Cancer Research, 59:2511-2515 (1999).
Taskeen, A. et al., "Analysis of bisphenol A in canned food: A mini review", Asian Journal of Chemistry, 22(5):4133-4135 (2010).
Thomson, A.A., "Role of androgens and fibroblast growth factors in prostatic development", Reproduction, 121:187-195 (2001).
Ueda, T. et al., "Activation of the Androgen Receptor N-terminal Domain by Interleukin-6 via MAPK and STAT3 Signal Transduction Pathways", The Journal of Biological Chemistry, 277(9):7076-7085 (2002).
Ueda, T. et al., "Ligand-independent Activation of the Androgen Receptor by Interleukin-6 and the Role of Steroid Receptor Coactivator-1 in Prostate cancer Cells", The Journal of Biological Chemistry, 277(41): 38087-38094 (2002).
Uematsu, Y. et al., "Chlorohydrins of bisphenol A diglycidyl ether (BADGE) and bisphenol F diglycidyl ether (BFDGE) in canned foods and ready-to-drink coffees from the Japanese market", Food Additives and Contaminants, 18(2):177-185 (2001).
Van Der Kwast, T.H. et al., "Androgen Receptors in Endocrine-Therapy-Resistant Human Prostate Cancer", Inter. J. Cancer, 48:189-193 (1991).
Van Scherpenzeel, M. et al., "Nanomolar affinity, iminosugar-based chemical probes for specific labeling of lysosomal glucocerebrosidase", Bioorganic & Medicinal Chemistry, 18:267-273 (2010).
Venkatesh, Srini, and Lipper, Robert A. "Role of the development scientist in compound lead selection and optimization." Journal of Pharmaceutical Sciences (2000); 89.2: 145-154.
Vippagunta et al., "Crystalline solids," Advanced Drug Delivery Reviews (2001) 48: 3-26.
Walfried et al., "Bisphenol F-Diglycidylether (BFDGE) und Folgeprodukte in Konservenfüllgütern: Synthese und Analytik," Deutsche Lebensmittel-Rundschau, vol. 96, No. 11, 2000, pp. 417-422 (with English abstract).
Wang, G. et al., "Identification of genes targeted by the androgen and PKA signaling pathways in prostate cancer cells", Oncogene, 25:7311-7323 (2006).
Wang, Q. et al., "Spatial and Temporal Recruitment of Androgen Receptor and Its Coactivators Involves Chromosomal Looping and Polymerase Tracking", Molecular Cell, 19:631-642 (2005).
Wetherill, Y. B. et al., "In vitro molecular mechanisms of bisphenol A action," Reproductive Toxicology, 24:178-198 (2007).
Wiedmann and Naqwi, "Pharmaceutical salts: Theory, use in solid dosage forms and in situ preparation in an aerosol." Asian Journal of Pharmaceutical Sciences (2016); 11(6): 722-734.
Wilcox and Cowart, "New Approaches to Synthetic Receptors. Synthesis and Host Properties of a Water Soluble Macrocyclic Analog of Troger's Base", Tetrahedron Letters, 27(46): 5563-5566 (1986).
Wilding, G., "The Importance of Steroid Hormones in Prostate Cancer", Cancer Surveys, 14:113-130 (1992).
Wilson, J.D. et al., "Long-Term Consequences of Castration in Men: Lessons from the Skoptzy and the Eunuchs of the Chinese and Ottoman Courts", The Journal of Clinical Endocrinology & Metabolism, 84:4324-4331 (1999).
Wolff (ed.) et al., Burger's Medicinal Chemistry and Drug Discovery, Fifth Edition, vol. I: Principles and Practice, 1995, pp. 975-977.
Wong, C. et al., "Steroid Requirement for Androgen Receptor Dimerization and DNA Binding", J. Bioi. Chem., 268(25):19004-19012 (1993).
Xu, X. et al., "Synthesis and Stability Study of Dental Monomers Containing Methacrylamidoethyl Phosphonic Acids", Journal of Polymer Science: Part A Polymer Chemistry, 45:99-110 (2007).
Yang et al., "Targeting Androgen Receptor Activation Function-1 with EPI to Overcome Resistance Mechanisms in Castration-Resistant Prostate Cancer," Clin Cancer Res; 22(17) Sep. 1, 2016, 4466-4477.
Ye, Deyong, "An Introduction to Computer-Aided Drug Design", 3 pages, Jan. 31, 2004 (non-English document).
Yonekubo, J. et al., "Concentrations of Bisphenol A, Bisphenol A Diglycidyl Ether, and Their Derivatives in Canned Foods in Japanese Markets," J. Agric. Food Chem., 2008, 56, 2041-2047.
Yong, Eu Leong, et al. "Molecular basis of androgen receptor diseases." Annals of Medicine (2000); 32.1: 15-22.
Zuhayra, M. et al., "New approach for the synthesis of [$^{18}$F]fluoroethyltyrosine for cancer imaging: Simple, fast, and high yielding automated synthesis", Bioorganic & Medicinal Chemistry, 17:7441-7448 (2009).
Extended European Search Report in Application No. EP 12768410.8 dated Sep. 22, 2014, 10 pages.
Extended European Search Report in Application No. EP 14793978.9 dated Sep. 1, 2016, 8 pages.
Supplementary European Search Report in EP Application No. 09771876.1 dated Jun. 20, 2011, 5 pages.
Supplementary European Search Report in EP Application No. 11731645.5 dated Jun. 20, 2013, 11 pages.
Extended European Search Report in Application No. EP 14843037.4 dated Mar. 8, 2017, 5 pages.
Extended European Search Report in Application No. EP 17177010.0 dated Oct. 20, 2017, 10 pages.
Extended European Search Report in Application No. 16736999.0 dated May 24, 2018, 14 pages.
Decision of Refusal for Japanese Application No. 2011-515039, dated Dec. 2, 2014, 18 pages (English translation).
International Search Report for International Application No. PCT/CA2009/000902 dated Sep. 1, 2009, 4 pages.
Written Opinion for International Application No. PCT/CA2009/000902 dated Sep. 1, 2009, 6 pages.

(56) References Cited

OTHER PUBLICATIONS

International Preliminary Report on Patentability for International Application No. PCT/CA2009/000902 dated Jan. 5, 2011, 7 pages.
International Search Report for International Application No. PCT/US2012/032584 dated Jul. 31, 2012, 3 pages.
Written Opinion for International Application No. PCT/US2012/032584 dated Jul. 31, 2012, 5 pages.
International Preliminary Report on Patentability for PCT/US2012/032584 dated Oct. 8, 2013, 6 pages.
International Search Report for International Application No. PCT/US2012/033959 dated Jul. 18, 2012, 3 pages.
Written Opinion for International Application No. PCT/US2012/033959 dated Jul. 18, 2012, 7 pages.
International Preliminary Report on Patentability for International Application No. PCT/US2012/033959 dated Oct. 22, 2013, 8 pages.
International Search Report for International Application No. PCT/US2012/033957 dated Jul. 18, 2012, 3 pages.
Written Opinion for International Application No. PCT/US2012/033957 dated Jul. 18, 2012, 5 pages.
International Preliminary Report on Patentability for International Application No. PCT/US2012/033957 dated Oct. 22, 2013, 6 pages.
International Search Report for International Application No. PCT/CA2011/000019 dated Mar. 21, 2011, 7 pages.
Written Opinion for International Application No. PCT/CA2011/000019 dated Mar. 21, 2011, 7 pages.
International Preliminary Report on Patentability for International Application No. PCT/CA2011/000019 dated Jul. 10, 2012, 8 pages.
International Search Report for International Application No. PCT/CA2011/000021 dated Apr. 18, 2011, 8 pages.
Written Opinion for International Application No. PCT/CA2011/000021 dated Apr. 18, 2011, 7 pages.
International Preliminary Report on Patentability for International Application No. PCT/CA2011/000021 dated Jul. 10, 2012, 8 pages.
International Search Report for International Application No. PCT/US2012/051481 dated Nov. 26, 2012, 4 pages.
Written Opinion for International Application No. PCT/US2012/051481 dated Nov. 26, 2012, 7 pages.
International Preliminary Report on Patentability for International Application No. PCT/US2012/051481 dated Feb. 25, 2014, 8 pages.
International Search Report for International Application No. PCT/US2012/051923 dated Jan. 28, 2013, 4 pages.
Written Opinion for International Application No. PCT/US2012/051923 dated Jan. 28, 2013, 8 pages.
International Preliminary Report on Patentability for International Application No. PCT/US2012/051923 dated Feb. 25, 2014, 9 pages.
International Search Report and Written Opinion for International Application No. PCT/CA2014/000414 dated Aug. 5, 2014, 6 pages.
International Preliminary Report on Patentability for International Application No. PCT/CA2014/000414 dated Nov. 10, 2015, 7 pages.
International Search Report and Written Opinion for International Application No. PCT/CA2014/000685 dated Dec. 4, 2014, 13 pages.
International Preliminary Report on Patentability for International Application No. PCT/CA2014/000685 dated Mar. 15, 2016, 7 pages.
International Search Report and Written Opinion for International Application No. PCT/CA2015/000533 dated Dec. 18, 2015, 11 pages.
International Preliminary Report on Patentability for International Application No. PCT/CA2015/000533 dated Apr. 18, 2017, 7 pages.
International Search Report and Written Opinion for International Application No. PCT/CA2015/000535 dated Dec. 23, 2015, 9 pages.
International Preliminary Report on Patentability for International Application No. PCT/CA2015/000535 dated Apr. 18, 2017, 6 pages.
International Search Report and Written Opinion for International Application No. PCT/CA2016/000008 dated Mar. 15, 2016, 13 pages.
International Preliminary Report on Patentability for International Application No. PCT/CA2016/000008 dated Jul. 18, 2017, 7 pages.
International Search Report and Written Opinion for International Application No. PCT/CA2016/000070 dated Jun. 2, 2016, 10 pages.
International Search Report and Written Opinion for International Application No. PCT/CA2017/000083 dated Aug. 3, 2017, 14 pages.
International Preliminary Report on Patentability for International Application No. PCT/CA2016/000070 dated Sep. 12, 2017, 6 pages.
International Search Report and Written Opinion for International Application No. PCT/CA2017/000141 dated Sep. 1, 2017, 11 pages.
International Search Report and Written Opinion for International Application No. PCT/CA2017/000201 dated Dec. 8, 2017, 9 pages.
International Search Report and Written Opinion for International Application No. PCT/US2019/057034 dated Feb. 6, 2020, 10 pages.
Aitipamula, S. et al. "Polymorphs, Salts, and Cocrystals: What's in a Name?", Crystal Growth & Design, 2012, 12(5), p. 2147-2152.
Auberson et al., "Ligand Specific Efficiency (LSE) Index for PET Tracer Optimization," ChemMedChem, vol. 11, No. 13, Jul. 5, 2016, pp. 1415-1427.
Extended European Search Report for European Application No. 19873360.2 dated Jun. 15, 2022, 10 pages.
International Search Report and Written Opinion for International Application No. PCT/US2022/025016, dated Jun. 29, 2022, 9 pages.
International Search Report and Written Opinion for Application No. PCT/US2022/026010, dated Aug. 26, 2022, 10 pages.
Osuka et al., "Synthesis and Photoexcited-State Dynamics of Aromatic Group-Bridged Carotenoid-Porphyrin Dyads and Carotenoid-Porphyrin-Pyromellitimide Triads," J. Am. Chem. Soc. 1993, 115, 9439-9452.
PubChem Compound Summary for CID 145662858, 1-Cyclobutyl-3-cyclopropylcyclobutane, Dec. 12, 2019, 7 pages.
PubChem Compound Summary for CID 146484310, 'N-[4-[[4-[2-[3-chloro-4-(2-chloroethoxy)-5-cyanophenyl]propan-2-yl]phenoxy]methyl]pyrimidin-2yl]methanesulfonamide', U.S. National Library of Medicine, Jun. 27, 2020, 8 pages; retrieved from https://pubchem.ncbi.nlm.nih.gov/compound/146484310.
Comstock et al., "Targeting cell cycle and hormone receptor pathways in cancer," Oncogene, 2013, vol. 32, pp. 5481-5491.
Reagan-Shaw S., et al. "Dose translation from animal to human studies revisited," The FASEB Journal, 2007, 22:659-661.

\* cited by examiner

BISPHENOL ETHER DERIVATIVES AND METHODS FOR USING THE SAME

CROSS-REFERENCE TO RELATED APPLICATION

This application is a divisional application of U.S. application Ser. No. 16/589,853, filed Oct. 1, 2019, which is a continuation application of U.S. application Ser. No. 15/557,726, filed Sep. 12, 2017, which is a U.S. National Stage Application under 35 U.S.C. § 371 of International Patent Application No. PCT/CA2016/000070, filed Mar. 11, 2016, which claims priority to U.S. Provisional Application No. 62/131,969 filed Mar. 12, 2015, the disclosures of each of which is herein incorporated by reference in its entirety for all purposes.

STATEMENT OF GOVERNMENT INTEREST

This invention was made with government support under R01 CA105304 awarded by the National Institutes of Health. The government has certain rights in the invention.

BACKGROUND

Technical Field

This invention generally relates to bisphenol-related compounds and their use for treatment of various indications. In particular the invention relates to bisphenol ether compounds having a chlorohydrin or a protected chlorohydrin moiety and their use for treatment of various cancers, for example all stages of prostate cancer, including androgen dependent, androgen sensitive and castration-resistant prostate cancers. This invention also relates to bisphenol-related compounds and their use for modulating androgen receptor (AR) activity.

Description of the Related Art

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Urol* 35, 355-361 (1999); A. A. Thomson, *Reproduction* 121, 187-195 (2001); N. Tanji, K. Aoki & M. Yokoyama, *Arch Androl* 47, 1-7 (2001)). Several lines of evidence show that androgens are associated with the development of prostate carcinogenesis. Firstly, androgens induce prostatic carcinogenesis in rodent models (R. L. Noble, *Cancer Res* 37, 1929-1933 (1977); R. L. Noble, *Oncology* 34, 138-141 (1977)) and men receiving androgens in the form of anabolic steroids have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 2365-2366 (1989); P. D. Guinan, W. Sadoughi, H. Alsheik, R. J. Ablin, D. Alrenga & I. M. Bush, *Am J Surg* 131, 599-600 (1976)). Secondly, prostate cancer does not develop if humans or dogs are castrated before puberty (J. D. Wilson & C. Roehrborn, *J Clin Endocrinol Metab* 84, 4324-4331 (1999); G. Wilding, *Cancer Surv* 14, 113-130 (1992)). Castration of adult males causes involution of the prostate and apoptosis of prostatic epithelium while eliciting no effect on other male external genitalia (E. M. Bruckheimer & N. Kyprianou, *Cell Tissue Res* 301, 153-162 (2000); J. T. Isaacs, *Prostate* 5, 545-557 (1984)). This dependency on androgens provides the underlying rationale for treating prostate cancer with chemical or surgical castration (androgen ablation).

Androgens also play a role in female diseases such as polycystic ovary syndrome as well as cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, *JAMA* 274, 1926-1930 (1995); R. J. Edmondson, J. M. Monaghan & B. R. Davies, *Br J Cancer* 86, 879-885 (2002)). The AR has been detected in a majority of ovarian cancers (H. A. Risch, *J Natl Cancer Inst* 90, 1774-1786 (1998); B. R. Rao & B. J. Slotman, *Endocr Rev* 12, 14-26 (1991); G. M. Clinton & W. Hua, *Crit Rev Oncol Hematol* 25, 1-9 (1997)), whereas estrogen receptor-alpha (ERa) and the progesterone receptor are detected in less than 50% of ovarian tumors.

The only effective treatment available for advanced prostate cancer is the withdrawal of androgens which are essential for the survival of prostate epithelial cells. Androgen ablation therapy causes a temporary reduction in tumor burden concomitant with a decrease in serum prostate-specific antigen (PSA). Unfortunately prostate cancer can eventually grow again in the absence of testicular androgens (castration-resistant disease) (Huber et al 1987 *Scand J Urol Nephrol.* 104, 33-39). Castration-resistant prostate cancer is biochemically characterized before the onset of symptoms by a rising titre of serum PSA (Miller et al 1992 *J. Urol.* 147, 956-961). Once the disease becomes castration-resistant most patients succumb to their disease within two years.

The AR has distinct functional domains that include the carboxy-terminal ligand-binding domain (LBD), a DNA-binding domain (DBD) comprising two zinc finger motifs, and an N-terminus domain (NTD) that contains one or more transcriptional activation domains. Binding of androgen (ligand) to the LBD of the AR results in its activation such that the receptor can effectively bind to its specific DNA consensus site, termed the androgen response element (ARE), on the promoter and enhancer regions of "normally" androgen regulated genes, such as PSA, to initiate transcription. The AR can be activated in the absence of androgen by stimulation of the cAMP-dependent protein kinase (PKA) pathway, with interleukin-6 (IL-6) and by various growth factors (Culig et al 1994 *Cancer Res.* 54, 5474-5478; Nazareth et al 1996 *J Biol. Chem.* 271, 19900-19907; Sadar 1999 *J Biol. Chem.* 274, 7777-7783; Ueda et al 2002 A *J. Biol. Chem.* 277, 7076-7085; and Ueda et al 2002 B *J Biol. Chem.* 277, 38087-38094). The mechanism of ligand-independent transformation of the AR has been shown to involve: 1) increased nuclear AR protein suggesting nuclear translocation; 2) increased AR/ARE complex formation; and 3) the AR-NTD (Sadar 1999 *J Biol. Chem.* 274, 7777-7783; Ueda et al 2002 A *J. Biol. Chem.* 277, 7076-7085; and Ueda et al 2002 B *J Biol. Chem.* 277, 38087-38094). The AR may be activated in the absence of testicular androgens by alternative signal transduction pathways in castration-resistant disease, which is consistent with the finding that nuclear AR protein is present in secondary prostate cancer tumors (Kim et al 2002 *Am. J. Pathol.* 160, 219-226; and van der Kwast et al 1991 *Inter. J. Cancer* 48, 189-193).

Available inhibitors of the AR include nonsteroidal antiandrogens such as bicalutamide (Casodex™), nilutamide, flutamide, enzulutamide and investigational drug ARN-509 and steroidal antiandrogens, such as cyproterone acetate.

These antiandrogens target the LBD of the AR and predominantly fail presumably due to poor affinity and mutations that lead to activation of the AR by these same antiandrogens (Taplin, M. E., Bubley, G. J., Kom Y. J., Small E. J., Uptonm M., Rajeshkumarm B., Balkm S. P., *Cancer Res.*, 59, 2511-2515 (1999)). These antiandrogens would also have no effect on the recently discovered AR splice variants that lack the ligand-binding domain (LBD) to result in a constitutively active receptor which promotes progression of castration recurrent prostate cancer (Dehm S M, Schmidt L J, Heemers H V, Vessella R L, Tindall D J., *Cancer Res* 68, 5469-77, 2008; Guo Z, Yang X, Sun F, Jiang R, Linn D E, Chen H, Chen H, Kong X, Melamed J, Tepper C G, Kung H J, Brodie A M, Edwards J, Qiu Y., *Cancer Res.* 69, 2305-13, 2009; Hu et al 2009 Cancer Res. 69, 16-22; Sun et al 2010 J Clin Invest. 2010 120, 2715-30).

Conventional therapy has concentrated on androgen-dependent activation of the AR through its C-terminal domain. Studies developing antagonists to the AR have concentrated on the C-terminus and specifically: 1) the allosteric pocket and AF-2 activity (Estébanez-Perpiñá et al 2007, *PNAS* 104, 16074-16079); 2) in silico "drug repurposing" procedure for identification of nonsteroidal antagonists (Bisson et al 2007, *PNAS* 104, 11927-11932); and coactivator or corepressor interactions (Chang et al 2005, *Mol Endocrinology* 19, 2478-2490; Hur et al 2004, *PLoS Biol* 2, E274; Estébanez-Perpiñá et al 2005, *JBC* 280, 8060-8068; He et al 2004, *Mol Cell* 16, 425-438).

The AR-NTD is also a target for drug development (e.g. WO 2000/001813), since the NTD contains Activation-Function-1 (AF-1) which is the essential region required for AR transcriptional activity (Jenster et al 1991. Mol Endocrinol. 5, 1396-404). The AR-NTD importantly plays a role in activation of the AR in the absence of androgens (Sadar, M. D. 1999 *J. Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 1860-9; Dehm et al 2006 *J Biol Chem.* 28, 27882-93; Gregory et al 2004 *J Biol Chem.* 279, 7119-30). The AR-NTD is important in hormonal progression of prostate cancer as shown by application of decoy molecules (Quayle et al 2007, *Proc Natl Acad Sci USA.* 104,1331-1336).

While the crystal structure has been resolved for the AR C-terminus LBD, this has not been the case for the NTD due to its high flexibility and intrinsic disorder in solution (Reid et al 2002 *J. Biol. Chem.* 277, 20079-20086) thereby hampering virtual docking drug discovery approaches. Compounds that modulate AR include the bis-phenol compounds disclosed in published PCT Nos: WO 2010/000066, WO 2011/082487; WO 2011/082488; WO 2012/145330; WO 2012/139039; WO 2012/145328; WO 2013/028572; WO 2013/028791; WO 2014/179867 and WO 2015/031984, which are hereby incorporated by reference in their entireties, to the British Columbia Cancer Agency Branch and The University of British Columbia.

BRIEF SUMMARY

The present disclosure is based in part on the discovery that the compounds described herein, may be used to modulate AR activity either in vivo or in vitro for both research and therapeutic uses. In accordance with one embodiment, there is provided a compound having a structure of Formula I:

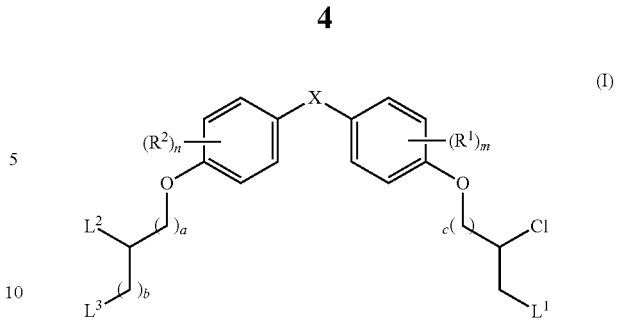

or a pharmaceutically acceptable salt, tautomer or stereoisomer thereof, wherein $R^1$, $R^2$, $L^1$, $L^2$, $L^3$, X, a, b, c, n, and m are as defined herein, are provided.

In other embodiments pharmaceutical compositions comprising a compound of Formula I are provided. Methods for modulating AR activity employing the present compounds and pharmaceutical compositions are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

I. Definitions

Figure 1A:
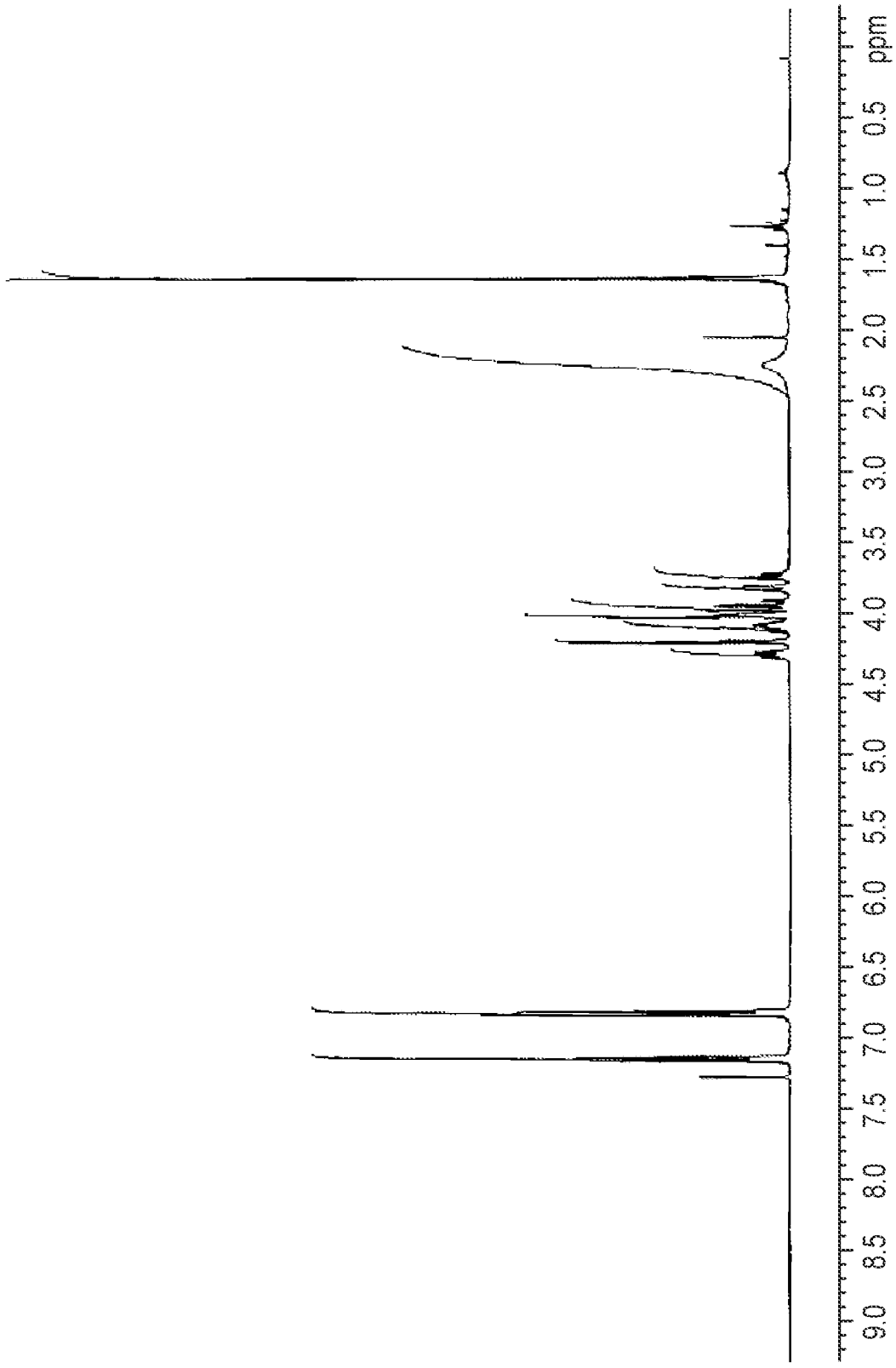
FIGS. 1A and 1B shows the $^1$H NMR (nuclear magnetic resonance spectroscopy) and the $^{13}$C NMR spectra for Compound 1a, respectively.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.

"Cyano" refers to the —CN radical.

"Halo" or "halogen" refers to bromo, chloro, fluoro or iodo radical. "Halo" or "halogen" can also refer to radioactive isotopes of the elements listed above, e.g., $^{123}$I and $^{18}$F.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, sec-propyl, n-butyl, i-butyl, sec-butyl, t-butyl, n-pentyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls.

Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)$R_a$ moiety, wherein $R_a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in $R_a$, as defined above. For example, "C1-$C_{10}$ acyl" refers to alkylcarbonyl group as defined above, where $R_a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" refers to a radical of the formula —$R_b$-$R_c$ where $R_b$ is an alkylene, alkenylene or alkynylene group as defined above and $R_c$ is one or more aryl radicals as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl. cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$-$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Chlorohydrin" refers to a radical having one of the following formulae:

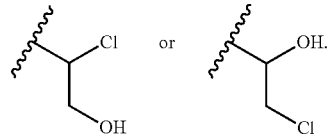 [SMILES: *C(Cl)CO ; *C(O)CCl]

"Protected chlorohydrin" refers to the above radical wherein the hydroxyl group is protected by a protecting group commonly known in the art to form, e.g., acetic acid ester (acetate), pivalic acid ester (pivalate) benzoid acid ester (benzoate), t-butyl ether, methoxymethyl ether, tetrahydropyranyl ether, allyl ether, benzyl ether, t-butyldimethylsilyl ether, t-butylphenylsilyl ether; (PG=protecting group):

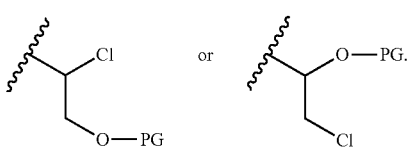

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable 3- to 20-membered non-aromatic ring radical which consists of two to twelve carbon atoms and from one to six heteroatoms selected from the group consisting of nitrogen, oxygen and sulfur. Heterocyclycl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heterocyclylalkyl" refers to a radical of the formula —$R_b$-$R_e$ where $R_b$ is an alkylene, alkenylene, or alkynylene chain as defined above and $R_e$ is a heterocyclyl radical as defined above, and if the heterocyclyl is a nitrogen-containing heterocyclyl, the heterocyclyl can be attached to the alkyl, alkenyl, alkynyl radical at the nitrogen atom. Unless stated otherwise specifically in the specification, a heterocyclylalkyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$-$R_f$ where $R_b$ is an alkylene, alkenylene, or alkynylene chain as defined above and $R_f$ is a heteroaryl radical as defined above. Unless stated otherwise specifically in the specification, a heteroarylalkyl group can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $NRgR_h$, $NR_gC(=O)R_h$, $NR_gC(=O)NR_gR_h$, $NR_gC(=O)OR_h$, $NR_gSO_2R_h$, $OC(=O)NR_gR_h$, $OR_g$, $SR_g$, $SORg$, $SO_2R_g$, $OSO_2R_g$, $SO_2OR_g$, =$NSO_2R_g$, and $SO_2NR_gR_h$. "Substituted also means any of the above groups in which one or more hydrogen atoms are replaced with C(=O)R$_g$, C(=O)OR$_g$, C(=O)NR$_g$R$_h$, CH$_2$SO$_2$R$_g$, CH$_2$SO$_2$NR$_g$R$_h$. In the foregoing, R$_g$ and R$_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

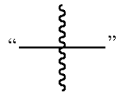

(hereinafter may be referred to as "a point of attachment bond") denotes a bond that is a point of attachment between two chemical entities, one of which is depicted as being attached to the point of attachment bond and the other of which is not depicted as being attached to the point of attachment bond. For example,

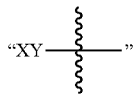

indicates that the chemical entity "XY" is bonded to another chemical entity via the point of attachment bond. Furthermore, the specific point of attachment to the non-depicted chemical entity may be specified by inference. For example, the compound CH$_3$-R$_j$, wherein R$_j$ is H or

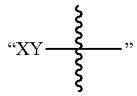

infers that when R$_j$ is "XY", the point of attachment bond is the same bond as the bond by which R$_j$ is depicted as being bonded to CH$_3$.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

As used herein, a "subject" may be a human, non-human primate, mammal, rat, mouse, cow, horse, pig, sheep, goat, dog, cat and the like. The subject may be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

An "effective amount" refers to a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to a castration-resistant form. Typically, a prophylactic dose is used in subjects prior to or at an earlier stage of disease, so that a prophylactically effective amount may be less than a therapeutically effective amount.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms whether or not they are specifically depicted herein. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the ACD/Name Version 9.07 software program, ChemDraw Ultra Version 11.0.1 and/or ChemDraw Ultra Version 14.0 software naming program (CambridgeSoft). For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

II. Compounds and Pharmaceutical Compositions

As noted above, certain embodiments of the present invention are directed to compounds useful for treatment of various cancers, including various types of prostate cancers. While not wishing to be bound by theory, it is believed that binding of the compounds to the androgen receptor (for example at the N-terminal domain) may contribute to the activity of the disclosed compounds. The compounds of the present invention relates to bisphenol ether compounds having a chlorohydrin or a protected chlorohydrin moiety which can impart improved properties to the compounds compared to compounds lacking the chlorohydrin or a protected chlorohydrin moiety (e.g., the right hand portion of a compound of Formula I). For example, the improved properties include improved drug-like properties such as improved activity (e.g., androgen receptor (AR) modulation), longer half-life (e.g., in vivo); decreased toxicity; better solubility, improved formulation, better bioavailability, better pharmacokinetic profile; reduction in unwanted metabolites and the like.

In one embodiment the invention includes compounds which can form covalent bonds with the androgen receptor (AR) (e.g., at the N-terminal domain), thus resulting in irreversible (or substantially irreversible) inhibition of the same. In this regard, the certain compounds of the present invention can be designed to include functional groups capable of forming covalent bonds with a nucleophile under certain in vivo conditions. For example, in some embodiments the reactivity of compounds of the present invention is such that they will not substantially react with various nucleophiles (e.g., glutathione) when the compounds are free in solution. However, when the free mobility of the compounds is restricted, and an appropriate nucleophile is brought into close proximity to the compound, for example when the compounds associate with, or bind to, the androgen receptor, the compounds can be capable of forming covalent bonds with certain nucleophiles (e.g., thiols).

The present invention includes all compounds which can have the above described properties (i.e., binding to androgen receptor (AR)). In one embodiment, the present invention is directed to a compound having a structure of Formula I:

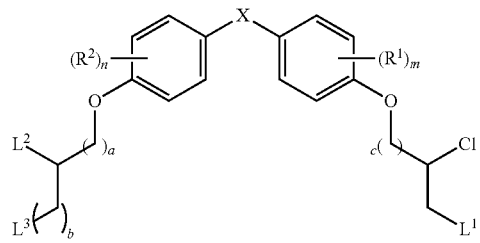

(I)

or a pharmaceutically acceptable salt, tautomer or stereoisomer thereof, wherein:

X is —O—, —S(O)$_{0-2}$—, —C(=O)—, —C(OR$^5$)$_2$—, —C(OR$^5$)(OC(=O)R$^{13}$)—, —C(R$^3$R$^4$)—, —C(=CR$^3$R$^4$)—, —N(R$^5$)—, —N(COR$^4$)—, —CHNR$^5$R$^6$—, —C(=NR$^5$)—, —C(=NOR$^5$)—, —C(=N—NHR$^7$)—;

R$^1$ and R$^2$ are each independently H, halogen, C$_1$-C$_{10}$ alkyl, C$_2$-C$_{10}$ alkenyl, C$_2$-C$_{10}$ alkynyl, —OH, —OR$^5$, —O(C$_1$-C$_6$)alkyl, —OC(=O)R$^{13}$, C$_1$-C$_{10}$ acyl, —S(O)$_{0-2}$R$^5$, —NO$_2$, —CN, —NH$_2$, —NHR$^5$, —N(R$^5$R$^6$), —CO$_2$H, —CO$_2$R$^{14}$, or —CONR$^5$R$^6$;

R$^3$ and R$^4$ are each independently H, halogen, —S(O)$_{0-2}$R$^{14}$, C$_1$-C$_{10}$ alkyl, C$_2$-C$_{10}$ alkenyl, C$_2$-C$_{10}$ alkynyl, aryl, aralkyl, C$_1$-C$_{10}$ acyl, or —NR$^5$R$^6$, or R$^3$ and R$^4$ may join to form a unsubstituted or substituted mono-, bi-, or tri-cyclic carbocycle or heterocycle containing from 3 to 20 carbon atoms;

R$^5$ and R$^6$ are each independently H, C$_1$-C$_{10}$ alkyl, C$_2$-C$_{10}$ alkenyl, or C$_2$-C$_{10}$ alkynyl;

R$^7$ is each independently H, C$_1$-C$_{10}$ alkyl, C$_2$-C$_{10}$ alkenyl, C$_2$-C$_{10}$ alkynyl, aryl, aminocarbonyl, C$_1$-C$_{10}$ alkylcarbonyl, C$_2$-C$_{10}$ alkenylcarbonyl, C$_2$-C$_{10}$ alkynylcarbonyl, C$_1$-C$_{10}$ alkylaminocarbonyl, C$_2$-C$_{10}$ alkenylaminocarbonyl, or C$_2$-C$_{10}$ alkynylaminocarbonyl;

R$^{13}$ is each independently C$_1$-C$_{10}$ alkyl, C$_2$-C$_{10}$ alkenyl, or C$_2$-C$_{10}$ alkynyl;

R$^{14}$ is each independently H, C$_1$-C$_{10}$ alkyl, C$_2$-C$_{10}$ alkenyl, C$_2$-C$_{10}$ alkynyl, or aryl;

L$^1$ is hydroxyl or —OC(=O)R$^{13}$;

L$^2$ and L$^3$ are each independently H, halogen, hydroxyl, —OC(=O)R$^{13}$, —OC$_1$-C$_{10}$ alkyl, —OC$_2$-C$_{10}$ alkenyl, —OC$_2$-C$_{10}$ alkynyl, —OR$^{15}$, —SR$^5$, —NR$^5$R$^6$, —O(C$_1$-C$_{10}$ acyl), —OC$_1$-C$_{10}$ alkylene-(—O—C$_1$-C$_{10}$ alkyl)$_p$, —OC$_1$-C$_{10}$ alkylene-(—O—C$_2$-C$_{10}$ alkynyl)$_p$, —OC$_1$-C$_{10}$ alkylene-(—O—C$_2$-C$_{10}$ alkenyl)$_p$, —OC$_2$-C$_{10}$ alkenylene-(—O—C$_1$-C$_{10}$ alkyl)$_p$, —OC$_2$-C$_{10}$ alkenylene-(—O—C$_2$-C$_{10}$ alkenyl)$_p$, —OC$_2$-C$_{10}$ alkenylene-(—O—C$_2$-C$_{10}$ alkynyl)$_p$, —OC$_2$-C$_{10}$ alkynylene-(—O—C$_1$-C$_{10}$ alkyl)$_p$, —OC$_2$-C$_{10}$ alkynylene-(—O—C$_1$-C$_{10}$ alkenyl)$_p$, —OC$_2$-C$_{10}$ alkynylene-(—O—C$_2$-C$_{10}$ alkynyl)$_p$, carbocyclyl, aryl, heterocyclyl, or heteroaryl;

R$^{15}$ is each independently selected from the group consisting of

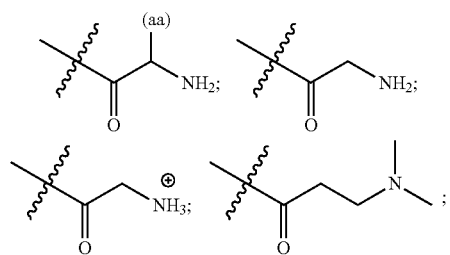

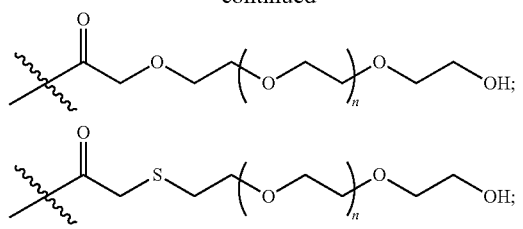
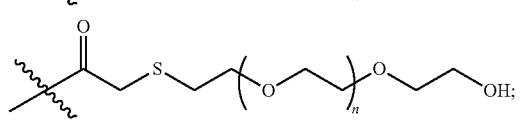
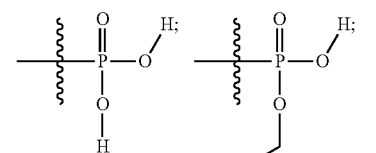
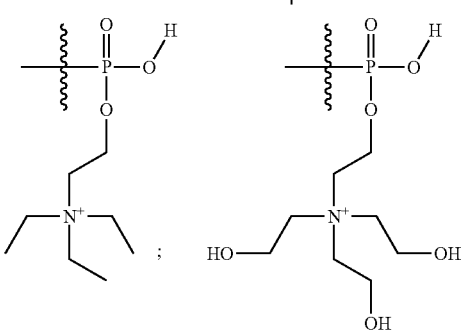
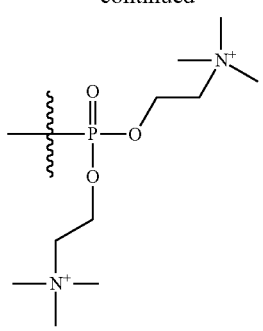
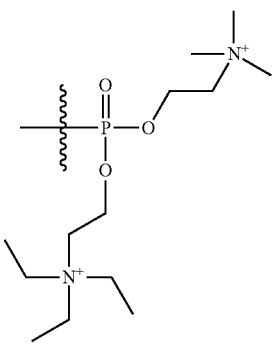
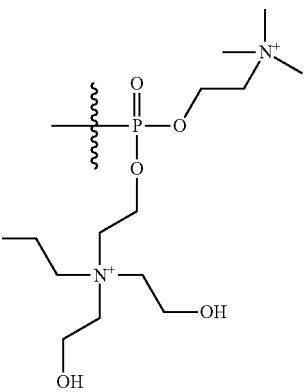
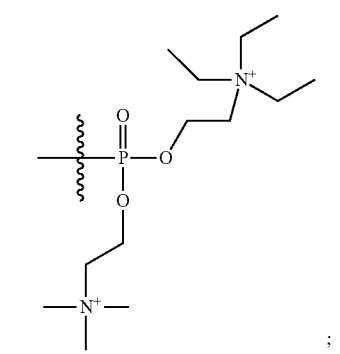

-continued

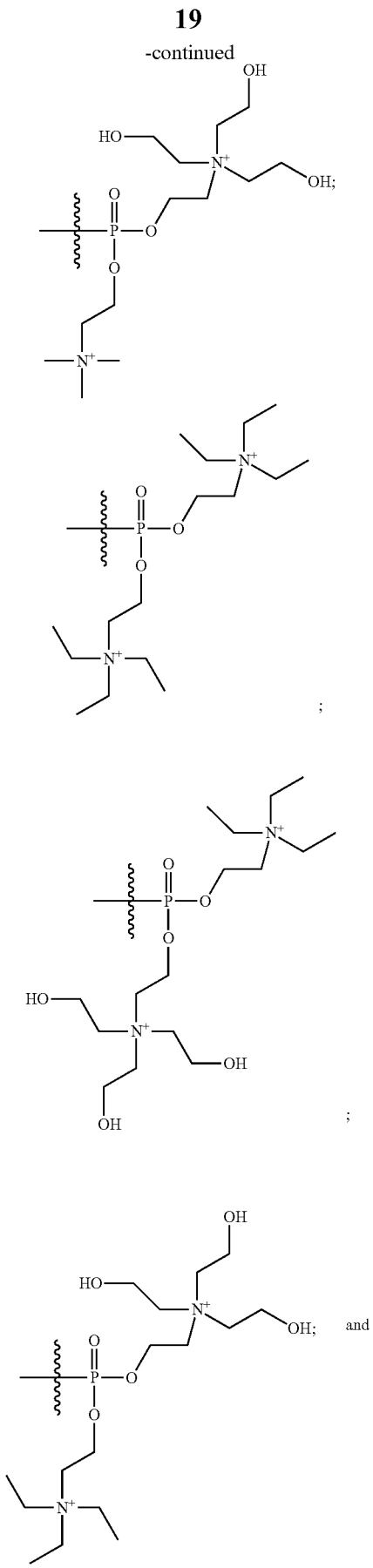

-continued

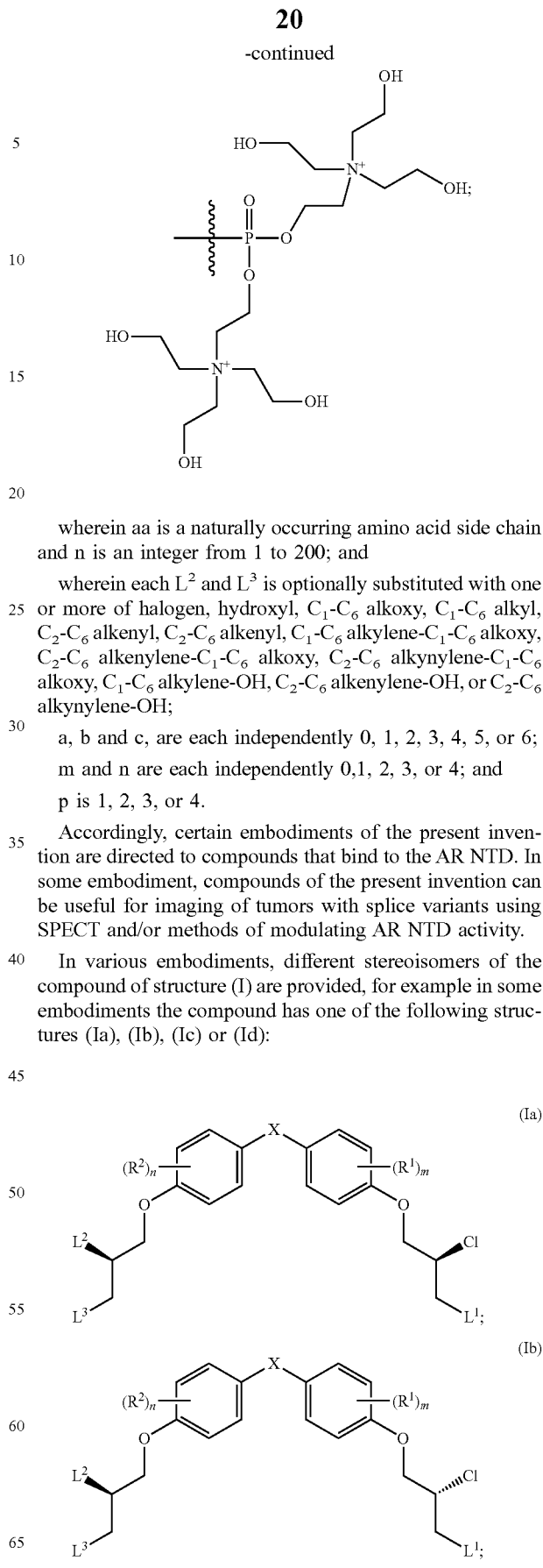

wherein aa is a naturally occurring amino acid side chain and n is an integer from 1 to 200; and wherein each $L^2$ and $L^3$ is optionally substituted with one or more of halogen, hydroxyl, $C_1$-$C_6$ alkoxy, $C_1$-$C_6$ alkyl, $C_2$-$C_6$ alkenyl, $C_2$-$C_6$ alkenyl, $C_1$-$C_6$ alkylene-$C_1$-$C_6$ alkoxy, $C_2$-$C_6$ alkenylene-$C_1$-$C_6$ alkoxy, $C_2$-$C_6$ alkynylene-$C_1$-$C_6$ alkoxy, $C_1$-$C_6$ alkylene-OH, $C_2$-$C_6$ alkenylene-OH, or $C_2$-$C_6$ alkynylene-OH;

a, b and c, are each independently 0, 1, 2, 3, 4, 5, or 6;

m and n are each independently 0,1, 2, 3, or 4; and p is 1, 2, 3, or 4.

Accordingly, certain embodiments of the present invention are directed to compounds that bind to the AR NTD. In some embodiment, compounds of the present invention can be useful for imaging of tumors with splice variants using SPECT and/or methods of modulating AR NTD activity.

In various embodiments, different stereoisomers of the compound of structure (I) are provided, for example in some embodiments the compound has one of the following structures (Ia), (Ib), (Ic) or (Id):

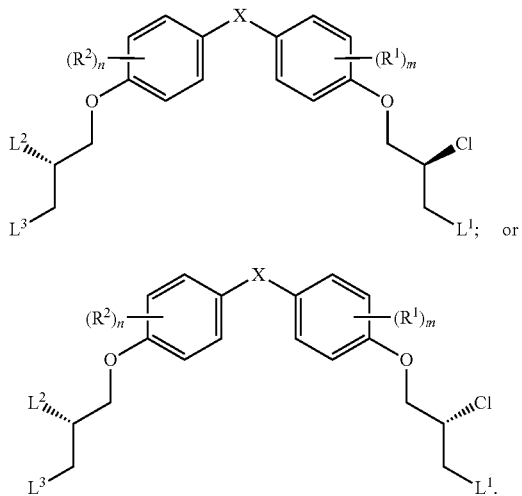

(Ic)

(Id)

In some embodiments, X is —O—. In other embodiments, X is —S(O)$_{0-2}$—. In some embodiments, X is —C(=O)—. In one embodiment, X is —C(OR$^5$)$_2$—. In one embodiment, X is —C(OR$^5$)(OC(=O)R$^{13}$)—. In some embodiments, X is —C(R$^3$R$^4$)—. In some embodiments, X is —C(=CR$^3$R$^4$)—. In other embodiments, X is —N(R$^5$)—. In one embodiment, X is —N(COR$^4$)—. In one embodiment, X is —CHNR$^5$R$^6$—. In another embodiment, X is —C(=NR$^5$)—. In some embodiments, X is —C(=NOR$^5$)—. In other embodiments, X is —C(=N—NHR$^7$)—.

In some embodiments, X is —C(R$^3$R$^4$)— wherein R$^3$ and R$^4$ are each independently H or C$_1$-C$_{10}$ alkyl. In other embodiments, X is —C(R$^3$R$^4$)— wherein R$^3$ and R$^4$ are each independently C$_1$-C$_{10}$ alkyl. In some embodiments, X is —C(R$^3$R$^4$)— wherein R$^3$ and R$^4$ are each independently C$_1$-C$_6$ alkyl. In some embodiments, X is —C(R$^3$R$^4$)— wherein R$^3$ and R$^4$ are each independently C$_1$-C$_5$ alkyl. In one embodiment, X is —C(R$^3$R$^4$)— wherein R$^3$ and R$^4$ are each independently C$_1$ alkyl. In another embodiment, X is —C(R$^3$R$^4$)— wherein R$^3$ and R$^4$ are each independently a methyl. In another embodiment, X is —C(R$^3$R$^4$)— wherein R$^3$ and R$^4$ are each C$_1$ alkyl, wherein R$^3$ and R$^4$ are joined together to form a cyclopropyl ring.

In certain embodiments, R$^1$ is each independently H, halogen, —O(C$_1$-C$_6$)alkyl, —O(C$_2$-C$_6$)alkenyl, —O(C$_2$-C$_6$) alkynyl, -C$_1$-C$_{10}$ alkyl, -C$_2$-C$_{10}$ alkenyl, -C$_2$-C$_{10}$ alkynyl, —OR$^5$—CO$_2$H, —CO2R$^{14}$, or —CONR$^5$R$^6$. In certain embodiments, R$^1$ is each independently H, halogen, —O(C$_1$-C$_6$)alkyl, —O(C$_2$-C$_6$)alkenyl, —O(C$_2$-C$_6$)alkynyl, -C$_1$-C$_{10}$ alkyl, -C$_2$-C$_{10}$ alkenyl, -C$_2$-C$_{10}$ alkynyl, or —OR$^5$. In another embodiment, R$^1$ is each independently H or halogen.

In certain embodiments, R$^2$ is each independently H, halogen, —O(C$_1$-C$_6$)alkyl, —O(C$_2$-C$_6$)alkenyl, —O(C$_2$-C$_6$) alkynyl, -C$_1$-C$_{10}$ alkyl, -C$_2$-C$_{10}$ alkenyl, -C$_2$-C$_{10}$ alkynyl, —OR$^5$—CO$_2$H, —CO$_2$R$^{14}$, or —CONR$^5$R$^6$. In certain embodiments, R$^2$ is each independently H, halogen, H, halogen, —O(C$_1$-C$_6$)alkyl, —O(C$_2$-C$_6$)alkenyl, —O(C$_2$-C$_6$) alkynyl, -C$_1$-C$_{10}$ alkyl, -C$_2$-C$_{10}$ alkenyl, -C$_2$-C$_{10}$ alkynyl, or —OR$^5$. In another embodiment, R$^2$ is each independently H or halogen.

In certain embodiments, R$^3$ and R$^4$ are each independently H, halogen, —S(O)$_{0-2}$R$^{14}$, C$_1$-C$_{10}$ alkyl, C$_2$-C$_{10}$ alkenyl, C$_2$-C$_{10}$ alkynyl, aryl, or aralkyl, C$_1$-C$_{10}$ acyl, or R$^3$ and R$^4$ may join to form a unsubstituted or substituted mono-, bi-, or tri-cyclic carbocycle or heterocycle containing from 3 to 20 carbon atoms.

In certain embodiments, R$^5$ and R$^6$ are each independently H, C$_1$-C$_6$ alkyl, C$_2$-C$_6$ alkenyl, or C$_2$-C$_6$ alkynyl. In some embodiments, when both R$^5$ and R$^6$ are present, R$^5$ is H and R$^6$ is C$_1$-C$_6$ alkyl, C$_2$-C$_6$ alkenyl, or C$_2$-C$_6$ alkynyl.

In certain embodiments, R$^7$ is each independently H, C$_1$-C$_6$ alkyl, C$_2$-C$_6$ alkenyl, C$_2$-C$_6$ alkynyl, or aryl.

In certain embodiments, R$^{14}$ is each independently H, C$_1$-C$_6$ alkyl, C$_2$-C$_6$ alkenyl, C$_2$-C$_6$ alkynyl, or aryl.

In certain embodiments, R$^{15}$ is each independently

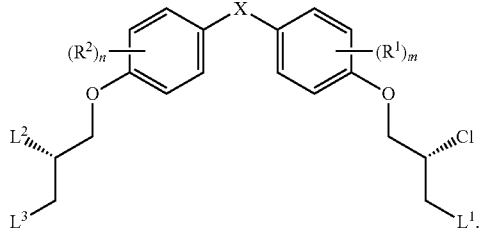

(aa)

In another embodiment, R$^{15}$ is each independently

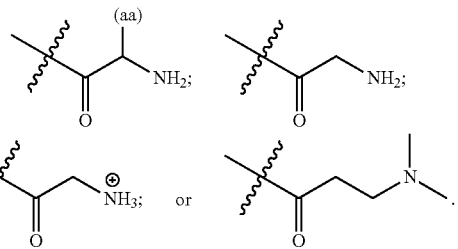

In some embodiments, R$^{15}$ is each independently

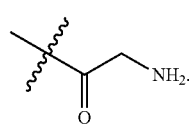 [SMILES: *C(=O)CN]

In certain of the foregoing embodiments, L$^1$ is hydroxyl or —OC(=O)R$^{13}$, wherein R$^{13}$ is -C$_1$-C$_{10}$ alkyl, -C$_2$-C$_{10}$ alkenyl or -C$_2$-C$_{10}$ alkynyl. In some embodiments, L$^1$ is hydroxyl. In another embodiment, L$^1$ is —OC(=O)C$_1$-C$_6$ alkyl. In one embodiment, L$^1$ is —OC(=O)C$_1$-C$_3$ alkyl. In some embodiments, L$^1$ is —OC(=O)CH$_3$.

In certain embodiments, L$^2$ and L$^3$ are each independently H, halogen, hydroxyl, —OC(=O)R$^{13}$, —OC$_1$-C$_{10}$ alkyl, —OC$_2$-C$_{10}$ alkenyl, —OC$_2$-C$_{10}$ alkynyl, —OR$^{15}$, —SR$^5$, —NR$^5$R$^6$, —O(C$_1$-C$_{10}$ acyl), carbocyclyl, aryl, heterocyclyl, or heteroaryl. In some embodiments, L$^2$ and L$^3$ are each independently H, halogen, hydroxyl, —OC(=O)R$^{13}$, —OC$_1$-C$_{10}$ alkyl, —OC$_2$-C$_{10}$ alkenyl, —OC$_2$-C$_{10}$ alkynyl, —OR$^{15}$, —SR$^5$, —NR$^5$R$^6$, or —O(C$_1$-C$_{10}$ acyl).

In certain of the foregoing embodiments, L$^2$ and L$^3$ are each independently H, hydroxyl, —OC$_1$-C$_{10}$ alkyl, -C$_2$-C$_{10}$ alkenyl, -C$_2$-C$_{10}$ alkynyl, or —OC(=O)R$^{13}$, wherein R$^{13}$ is -C$_1$-C$_{10}$ alkyl, -C$_2$-C$_{10}$ alkenyl or -C$_2$-C$_{10}$ alkynyl. In some embodiments, at least one of L$^2$ and L$^3$ is a hydroxyl. In another embodiment, at least one of L$^2$ and L$^3$ is a —OC$_1$-C$_{10}$ alkyl or —OC(=O)C$_1$-C$_{10}$ alkyl. In a further embodiment, L$^2$ or L$^3$ is a hydroxyl and the remainder is —OC$_1$-C$_{10}$ alkyl or —OC(=O)C$_1$-C$_{10}$ alkyl.

In another embodiment, at least one of $L^2$ and $L^3$ is a carbocyclyl, aryl, heterocyclyl, or heteroaryl. In one embodiment, at least one of $L^2$ and $L^3$ is heterocyclyl or heteroaryl. In some embodiment, at least one of $L^2$ and $L^3$ is 3-7 membered heterocylyl, wherein said heteroaryl or said heterocyclyl comprises at least one N atom in the ring.

In another embodiment, at least one of $L^2$ and $L^3$ is selected from a group consisting of pyrrole, furan, thiophene, pyrazole, pyridine, pyridazine, pyrimidine, imidazole, thiazole, isoxazole, oxadiazole, thiadiazole, oxazole, triazole, isothiazole, oxazine, triazine, azepine, pyrrolidine, pyrroline, imidazoline, imidazolidine, pyrazoline, pyrazolidine, piperidine, dioxane, morpholine, dithiane, thiomorpholine, piperazine, and tetrazine.

In one embodiment, n is 0, 1, or 2. In another embodiment, n is 0 or 1.

In one embodiment, m is 0, 1, or 2. In another embodiment, m is 0 or 1.

In some embodiment, a is 0, 1, 2, or 3. In another embodiment, a is 0, 1, or 2. In one embodiment, a is 1.

In some embodiment, b is 0, 1, 2, or 3. In another embodiment, b is 0, 1, or 2. In one embodiment, b is 1.

In some embodiment, c is 0, 1, 2, or 3. In another embodiment, c is 0, 1, or 2. In one embodiment, c is 1.

In one embodiment, the compound of Formula I comprising one or more halogens which can be radioactive isotopes of said halogens.

In some more specific embodiments of the compound of Formula I, the compound has one of the following structures from Table 1, or a pharmaceutically acceptable salt, tautomer, or stereoisomer thereof:

TABLE 1

Representative Compounds

| No. | Structure | Name |
|---|---|---|
| 1 | 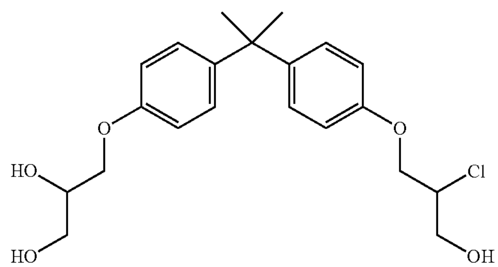 [SMILES: CC(C)(c1ccc(OCC(O)CO)cc1)c1ccc(OCC(Cl)CO)cc1] | 3-(4-(2-(4-(2-chloro-3-hydroxypropoxy)phenyl)propan-2-yl)phenoxy)propane-1,2-diol |
| 1a | 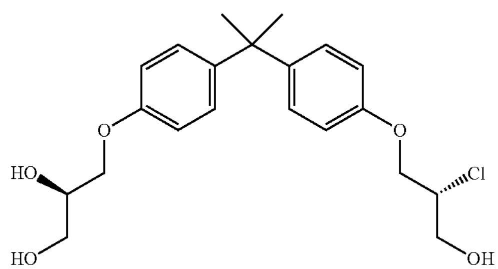 | (R)-3-(4-(2-(4-((R)-2-chloro-3-hydroxypropoxy)phenyl)propan-2-yl)phenoxy)propane-1,2-diol |
| 1b | 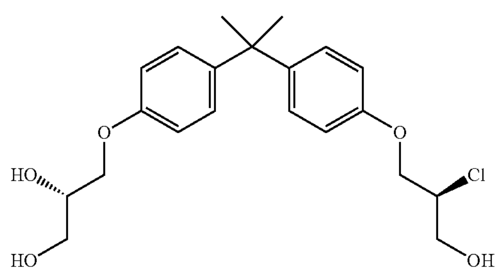 [SMILES: CC(C)(c1ccc(OC[C@@H](O)CO)cc1)c1ccc(OC[C@@H](Cl)CO)cc1] | (S)-3-(4-(2-(4-((S)-2-chloro-3-hydroxypropoxy)phenyl)propan-2-yl)phenoxy)propane-1,2-diol |
| 1c | 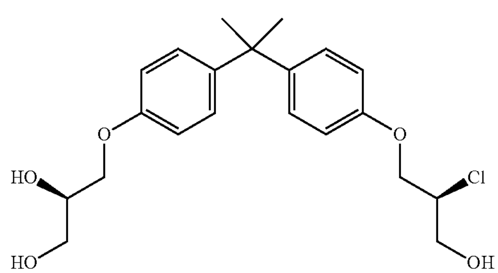 [SMILES: CC(C)(c1ccc(OC[C@H](O)CO)cc1)c1ccc(OC[C@@H](Cl)CO)cc1] | (R)-3-(4-(2-(4-((S)-2-chloro-3-hydroxypropoxy)phenyl)propan-2-yl)phenoxy)propane-1,2-diol |

TABLE 1-continued

Representative Compounds

| No. | Structure | Name |
|---|---|---|
| 1d | 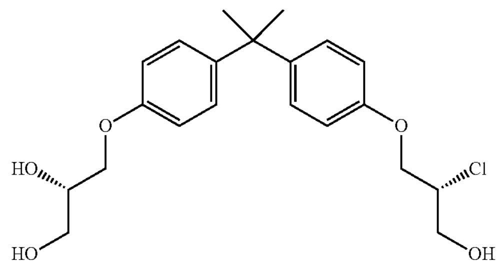 | (S)-3-(4-(2-(4-((R)-2-chloro-3-hydroxypropoxy)phenyl)propan-2-yl)phenoxy)propane-1,2-diol |
| 2 | 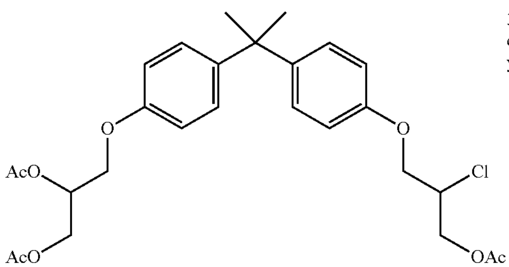 | 3-(4-(2-(4-(3-acetoxy-2-chloropropoxy)phenyl)propan-2-yl)phenoxy)propane-1,2-diyl diacetate |
| 2a | 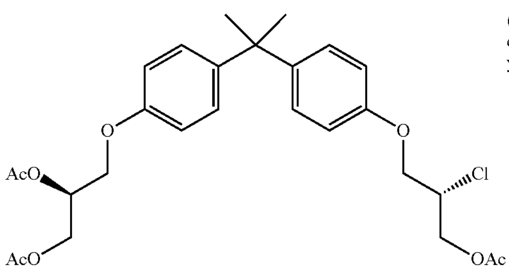 | (S)-3-(4-(2-(4-(S))-3-acetoxy-2-chloropropoxy)phenyl)propan-2-yl)phenoxy)propane-1,2-diyl diacetate |
| 2b | 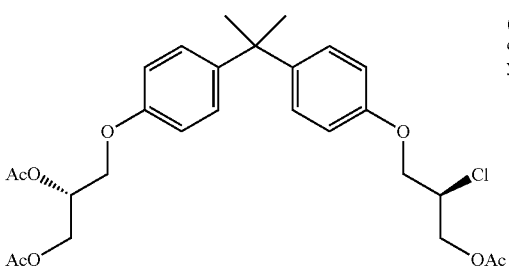 | (R)-3-(4-(2-(4-((R)-3-acetoxy-2-chloropropoxy)phenyl)propan-2-yl)phenoxy)propane-1,2-diyl diacetate |
| 2c | 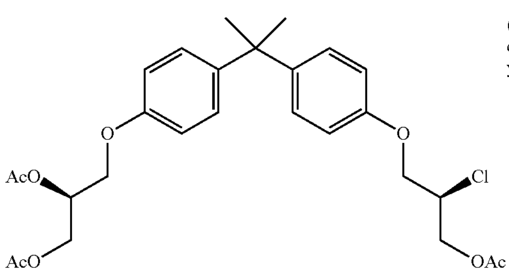 | (S)-3-(4-(2-(4-((R)-3-acetoxy-2-chloropropoxy)phenyl)propan-2-yl)phenoxy)propane-1,2-diyl diacetate |

| No. | Structure | Name |
|---|---|---|
| 2d | 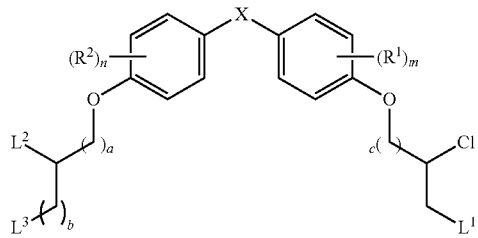 | (R)-3-(4-(2-(4-((S)-3-acetoxy-2-chloropropoxy)phenyl)propan-2-yl)phenoxy)propane-1,2-diyl diacetate |

In one embodiment, the present invention is directed to a pharmaceutical composition, comprising a compound having a structure of Formula I:

$$\text{(I)}$$

(R²)ₙ and (R¹)ₘ substituted diphenyl-X core with L², L³ and L¹ substituents as drawn or a pharmaceutically acceptable salt, tautomer or stereoisomer thereof, wherein:

X is —O—, —S(O)$_{0-2}$—, —C(=O)—, —C(OR⁵)₂—, —C(OR⁵)(OC(=O)R¹³)—, —C(R³R⁴)—, —C(=CR³R⁴)—, —N(R⁵)—, —N(COR⁴)—, —CHNR⁵R⁶—, —C(=NR⁵)—, —C(=NOR⁵)—, —C(=N—NHR⁷)—;

R¹ and R² are each independently H, halogen, $C_1$-$C_{10}$ alkyl, $C_2$-$C_{10}$ alkenyl, $C_2$-$C_{10}$ alkynyl, —OH, —OR⁵, —O($C_1$-$C_6$)alkyl, —OC(=O)R¹³, $C_1$-$C_{10}$ acyl, —S(O)$_{0-2}$R⁵, —NO₂, —CN, —NH₂, —NHR⁵, —N(R⁵R⁶), —CO₂H, CO₂R¹⁴, or CONR⁵R⁶;

R³ and R⁴ are each independently H, halogen, —S(O)$_{0-2}$R¹⁴, $C_1$-$C_{10}$ alkyl, $C_2$-$C_{10}$ alkenyl, $C_2$-$C_{10}$ alkynyl, aryl, aralkyl, $C_1$-$C_{10}$ acyl, or —NR⁵R⁶, or R³ and R⁴ may join to form a unsubstituted or substituted mono-, bi-, or tri-cyclic carbocycle or heterocycle containing from 3 to 20 carbon atoms;

R⁵ and R⁶ is each independently H, $C_1$-$C_{10}$ alkyl, $C_2$-$C_{10}$ alkenyl, or $C_2$-$C_{10}$ alkynyl;

R⁷ is each independently H, $C_1$-$C_{10}$ alkyl, $C_2$-$C_{10}$ alkenyl, $C_2$-$C_{10}$ alkynyl, aryl, aminocarbonyl, $C_1$-$C_{10}$ alkylcarbonyl, $C_2$-$C_{10}$ alkenylcarbonyl, $C_2$-$C_{10}$ alkynylcarbonyl, $C_1$-$C_{10}$ alkylaminocarbonyl, $C_2$-$C_{10}$ alkenylaminocarbonyl, or $C_2$-$C_{10}$ alkynylaminocarbonyl;

R¹³ is each independently $C_1$-$C_{10}$ alkyl, $C_2$-$C_{10}$ alkenyl, or $C_2$-$C_{10}$ alkynyl;

R¹⁴ is each independently H, $C_1$-$C_{10}$ alkyl, $C_2$-$C_{10}$ alkenyl, $C_2$-$C_{10}$ alkynyl, or aryl;

L¹ is hydroxyl or —OC(=O)R¹³;

L² and L³ are each independently H, halogen, hydroxyl, —OC(=O)R¹³, —OC$_1$-$C_{10}$ alkyl, —OC$_2$-$C_{10}$ alkenyl, —OC$_2$-$C_{10}$ alkynyl, —OR¹⁵, —SR⁵, —NR⁵R⁶, —O($C_1$-$C_{10}$ acyl), —OC$_1$-$C_{10}$ alkylene-(—O—$C_1$-$C_{10}$ alkyl)$_p$, —OC$_1$-$C_{10}$ alkylene-(—O—$C_2$-$C_{10}$ alkynyl)$_p$, —OC$_1$-$C_{10}$ alkylene-(—O—$C_2$-$C_{10}$ alkenyl)$_p$, —OC$_2$-$C_{10}$ alkenylene-(—O—$C_1$-$C_{10}$ alkyl)$_p$, —OC$_2$-$C_{10}$ alkenylene-(—O—$C_2$-$C_{10}$ alkenyl)$_p$, —OC$_2$-$C_{10}$ alkenylene-(—O—$C_2$-$C_{10}$ alkynyl)$_p$, —OC$_2$-$C_{10}$ alkynylene-(—O—$C_1$-$C_{10}$ alkyl)$_p$, —OC$_2$-$C_{10}$ alkynylene-(—O—$C_1$-$C_{10}$ alkenyl)$_p$, —OC$_2$-$C_{10}$ alkynylene-(—O—$C_2$-$C_{10}$ alkynyl)$_p$, carbocyclyl, aryl, heterocyclyl, or heteroaryl;

R¹⁵ is each independently selected from the group consisting of

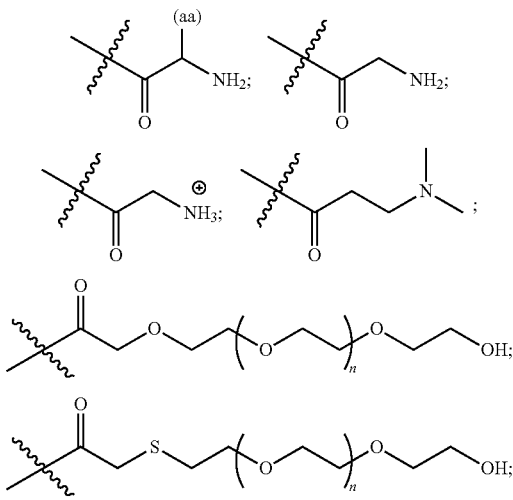

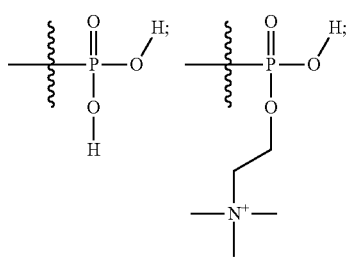

29
-continued
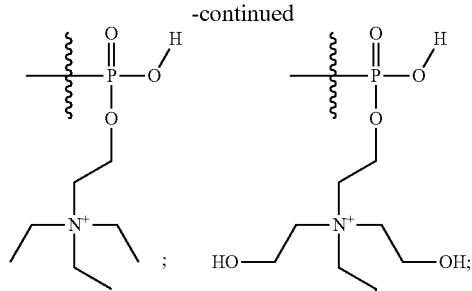
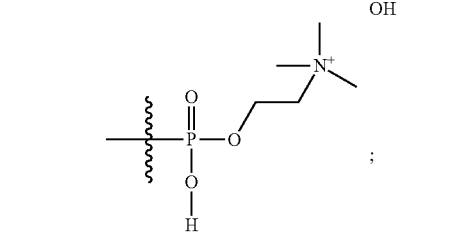
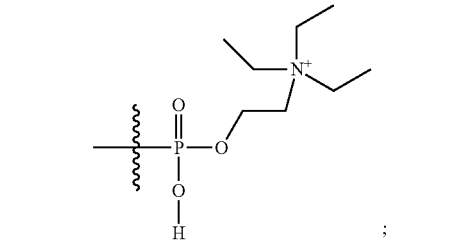
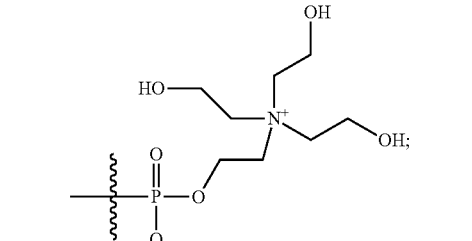
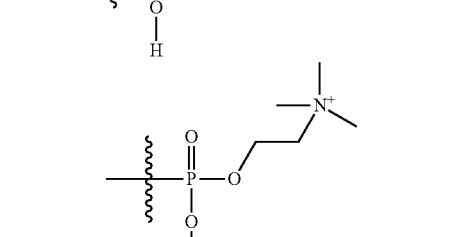
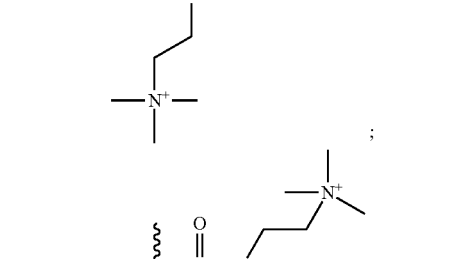
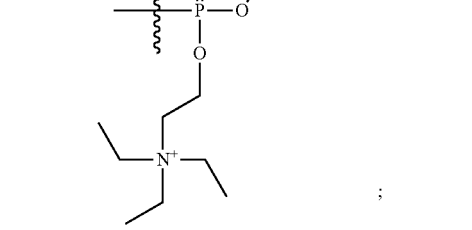
30
-continued
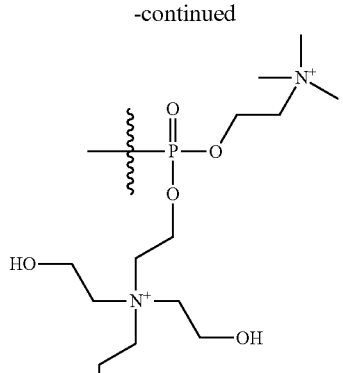
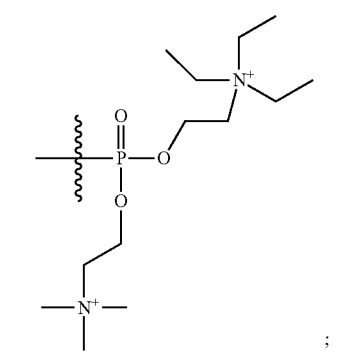
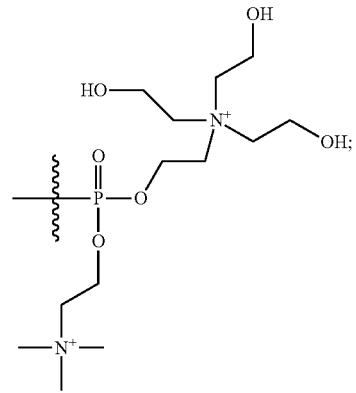
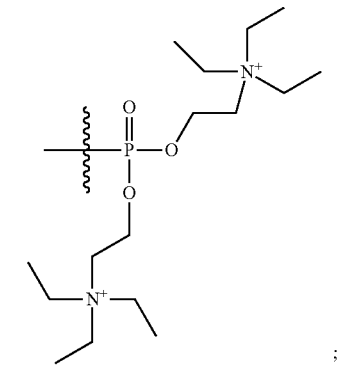

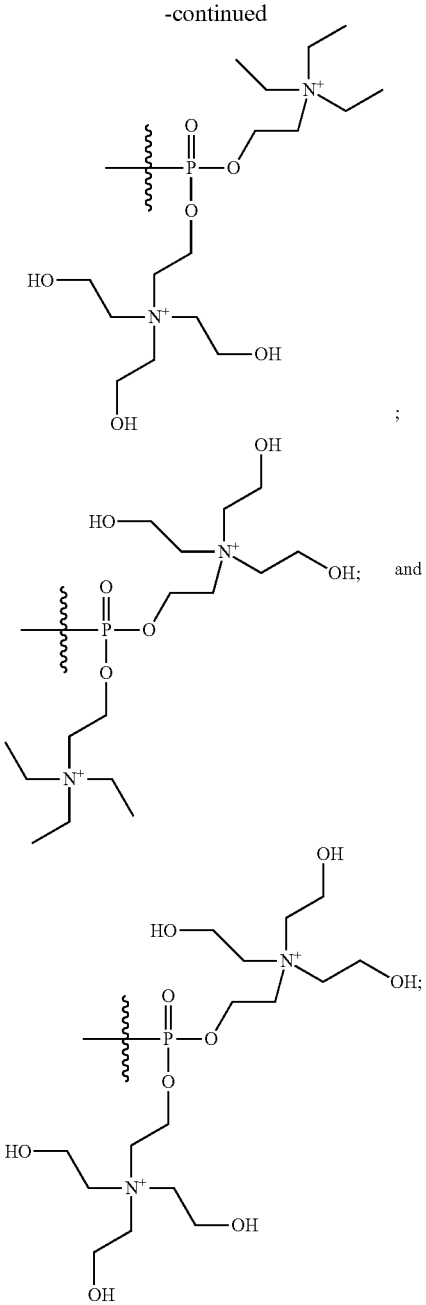

wherein aa is a naturally occurring amino acid side chain and n is an integer from 1 to 200, and wherein each $L^2$ and $L^3$ is optionally substituted with one or more of halogen, hydroxyl, $C_1$-$C_6$ alkoxy, $C_1$-$C_6$ alkyl, $C_2$-$C_6$ alkenyl, $C_2$-$C_6$ alkenyl, $C_1$-$C_6$ alkylene-$C_1$-$C_6$ alkoxy, $C_2$-$C_6$ alkenylene-$C_1$-$C_6$ alkoxy, $C_2$-$C_6$ alkynylene-$C_1$-$C_6$ alkoxy, $C_1$-$C_6$ alkylene-OH, $C_2$-$C_6$ alkenylene-OH, or $C_2$-$C_6$ alkynylene-OH;

a, b and c, are each independently 0, 1, 2, 3, 4, 5, or 6;
m and n are each independently 0, 1, 2, 3, or 4; and
p is 1, 2, 3, or 4.

In some embodiment, the pharmaceutical composition comprising a compound having a structure of Formula I can further comprise a pharmaceutically acceptable carrier. In another embodiment, the pharmaceutical composition comprising a compound having a structure of Formula I can further comprise an additional therapeutic agent. In one embodiment, the pharmaceutical composition comprising a compound having a structure of Formula I can further comprise a pharmaceutically acceptable carrier and an additional therapeutic agent.

In another embodiment, the pharmaceutical composition comprising a compound having a structure of Formula I can further comprise an additional therapeutic agent which is for treating prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, age-related macular degeneration, or combinations thereof.

Accordingly, one embodiment comprises the use of the disclosed compounds in combination therapy with one or more currently-used or experimental pharmacological therapies which are utilized for treating the above disease states irrespective of the biological mechanism of action of such pharmacological therapies, including without limitation pharmacological therapies which directly or indirectly inhibit the androgen receptor, pharmacological therapies which are cyto-toxic in nature, and pharmacological therapies which interfere with the biological production or function of androgen (hereinafter, an "additional therapeutic agent"). By "combination therapy" is meant the administration of any one or more of a compound of Formula I with one or more of another therapeutic agent to the same patient such that their pharmacological effects are contemporaneous with one another, or if not contemporaneous, that their effects are synergistic with one another even though dosed sequentially rather than contemporaneously.

Such administration can include without limitation dosing of one or more of a compound of Formula I and one or more of the additional therapeutic agent(s) as separate agents without any comingling prior to dosing, as well as formulations which include one or more other androgen-blocking therapeutic agents mixed with one or more compound of Formula I as a pre-mixed formulation. Administration of the compound(s) of Formula I in combination with the additional therapeutic agents for treatment of the above disease states can also include dosing by any dosing method including without limitation, intravenous delivery, oral delivery, intra-peritoneal delivery, intra-muscular delivery, or intra-tumoral delivery.

In another aspect of the present disclosure, the one or more of the additional therapeutic agents can be administered to the patient before administration of the compound(s) of Formula I. In another embodiment, the compound(s) of Formula I can be co-administered with one or more of the additional therapeutic agents. In yet another aspect, the one or more additional therapeutic agents can be administered to the patient after administration of the compound(s) of Formula I.

It is fully within the scope of the disclosure that the ratio of the doses of compound(s) of Formula I to that of the one or more additional therapeutic agents may or may not equal to one and can be varied accordingly to achieve the optimal therapeutic benefit.

For greater clarity the compound(s) of Formula I that are combined with the one or more additional therapeutic agents for improved treatment of the above disease states can comprise, but are not limited to any compound having a structure of Formula I, including those compounds shown in Table 1.

The additional therapeutic agents include without limitation any pharmacological agent which is currently approved by the FDA in the U.S. (or elsewhere by any other regulatory body) for use as pharmacological treatment of any of the above disease states, or which is currently being used experimentally as part of a clinical trial program that relates to the above disease states. Non-limiting examples of the other pharmacological agents can comprise, without limitation: the chemical entity known as ODM-201 (also known as BAY1841788) and related compounds;, which appears to bind to the AR and blocks its cellular function, and is currently in clinical development as a treatment for prostate cancer); the chemical entity known as enzalutamide (4-(3-(4-cyano-3-(trifluoromethyl)phenyl)-5,5-dimethyl-4-oxo-2-thioxoimidazolidin-1-yl)-2-fluoro-N-methylbenzamide) and related compounds, which appears to be a blocker of the androgen receptor (AR) LBD and a FDA-approved treatment for prostate cancer; the chemical entity known as Galeterone and related compounds which appears to be a blocker of the androgen receptor (AR) LBD, and a CYP17 lyase inhibitor, and also appears to decrease overall androgen receptor levels in prostate cancer cells. Galeterone is currently in development as a treatment for prostate cancer; the chemical entity known as ARN-509 (4-[7-[6-cyano-5-(trifluoromethyl)pyridin-3-yl]-8-oxo-6-sulfanylidene-5,7-diazaspiro[3.4]octan-5-yl]-2-fluoro-N-methylbenzamide) and related compounds which appears to be a blocker of the androgen receptor (AR) LBD and is currently in development as a treatment for prostate cancer; the chemical entity known as abiraterone (or CB-7630; (3S,8R,9S,10R,13S,14S)-10,13-dimethyl-17-(pyridin-3 -yl) 2,3,4,7,8,9,10,11,12,13,14,15-dodecahydro-1H-cyclopenta[a]phenanthren-3-ol), and related molecules, which appears to block the production of androgen and FDA-approved treatment for prostate cancer; the chemical entity known as bicalutamide (N-[4-cyano-3-(trifluoromethyl)phenyl]-3-[(4-fluorophenyl)sulfonyl]-2-hydroxy-2-methylpropanamide) and related compounds, which appears to be a blocker of the androgen receptor (AR) LBD and which is currently used to treat prostate cancer, the chemical entity known as nilutamide (5,5-dimethyl-3-[4-nitro-3-(trifluoromethyl)phenyl] imidazolidine-2,4-dione) and related compounds, which appears to be a blocker of the AR LBD and which is currently used to treat prostate cancer, the chemical entity known as flutamide (2-methyl-N-[4-nitro-3-(trifluoromethyl)phenyl]-propanamide) and related compounds, which appears to be a blocker of the androgen receptor (AR) LBD and which is currently used to treat prostate cancer, the chemical entities known as cyproterone acetate (6-chloro-1β,2β-dihydro-17-hydroxy-3'H-cyclopropa[1,2]pregna-4,6-diene-3,20-dione) and related compounds, which appears to be a blocker of the androgen receptor (AR) LBD and which is currently used to treat prostate cancer, the chemical entity known as docetaxel (Taxotere; 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}) and related compounds, which appears to be a cytotoxic antimicrotubule agent and is currently used in combination with prednisone to treat prostate cancer, the chemical entity known as Bevacizumab (Avastin), a monoclonal antibody that recognizes and blocks vascular endothelial growth factor A (VEGF-A) and may be used to treat prostate cancer, the chemical entity known as OSU-HDAC42 ((S)-(+)-N-hydroxy-4-(3-methyl-2-phenylbutyrylamino)-benzamide), and related compounds, which appears to act as a histone deacetylase inhibitor, and is currently being developed as a treatment for prostate cancer, the chemical entity known as VITAXIN which appears to be a monoclonal antibody against the vascular integrin αvβ3 to prevent angiogenesis, and which may be used to treat prostate cancer, the chemical entity known as sunitumib (N-(2-diethylaminoethyl)-5-[(Z)-(5-fluoro-2-oxo-1H-indol-3-ylidene)methyl]-2,4-dimethyl-1H-pyrrole-3-carboxamide) and related compounds, which appears to inhibit multiple receptor tyrosine kinases (RTKs) and may be used for treatment of prostate cancer, the chemical entity known as ZD-4054 (N-(3-Methoxy-5-methylpyrazin-2-yl)-2-[4-(1,3,4-oxadiazol-2-yl)phenyl]pyridin-3-sulfonamid) and related compounds, which appears to block the edta receptor and which may be used for treatment of prostate cancer; the chemical entity known as Cabazitaxel (XRP-6258), and related compounds, which appears to be a cytotoxic microtubule inhibitor, and which is currently used to treat prostate cancer; the chemical entity known as MDX-010 (Ipilimumab), a fully human monoclonal antibody that binds to and blocks the activity of CTLA-4 which is currently in development as an immunotherapeutic agent for treatment of prostate cancer; the chemical entity known as OGX 427 which appears to target HSP27 as an antisense agent, and which is currently in development for treatment of prostate cancer; the chemical entity known as OGX 011 which appears to target clusterin as an antisense agent, and which is currently in development as a treatment for prostate cancer; the chemical entity known as finasteride (Proscar, Propecia; N-(1,1-dimethylethyl)-3-oxo-(5α,17β)-4-azaandrost-1-ene-17-carboxamide), and related compounds, which appears to be a 5-alpha reductase inhibitor that reduces levels of dihydrotestosterone, and may be used to treat prostate cancer; the chemical entity known as dutasteride (Avodart; 5α, 17β)-N-{2,5bis(trifluoromethyl) phenyl}-3-oxo-4-azaandrost-1-ene-17-carboxamide) and related molecules, which appears to be a 5-alpha reductase inhibitor that reduces levels of dihydrotestosterone, and may be used in the treatment of prostate cancer; the chemical entity known as turosteride ((4aR,4bS,6aS,7S,9aS,9bS,11aR)-1,4a,6a-trimethyl-2-oxo-N-(propan-2-yl)-N-(propan-2 ylcarbamoyl)hexadecahydro-1H-indeno[5,4-f]quinoline-7-carboxamide), and related molecules, which appears to be a 5-alpha reductase inhibitor that reduces levels of dihydrotestosterone and may be used in the treatment of prostate cancer; the chemical entity known as bexlosteride (LY-191,704; (4aS,10bR)-8-chloro-4-methyl-1,2,4a,5,6,10b-hexahydrobenzo[f]quinolin-3 -one), and related compounds, which appears to be a 5-alpha reductase inhibitor that reduces levels of dihydrotestosterone and may be used in the treatment of prostate cancer; the chemical entity known as izonsteride (LY-320,236; (4aR,10bR)-8-[(4-ethyl-1,3-benzothiazol-2-yl)sulfanyl]-4,10b-dimethyl-1,4,4a,5,6,10b-hexahydrobenzo[f]quinolin-3 (2H)-one) and related compounds, which appears to be a 5-alpha reductase inhibitor that reduces levels of dihydrotestosterone and may be used for the treatment of prostate cancer; the chemical entity known as FCE 28260 and related compounds, which appears to be a 5-alpha reductase inhibitor that reduces levels of dihydrotestosterone and may be used for the treatment of prostate cancer; the chemical entity known as SKF105,111, and related compounds, which appears to be a 5-alpha reductase inhibitor that reduces levels of dihydrotestosterone and may be used for treatment of prostate cancer.

Accordingly, in some embodiments, the pharmaceutical composition comprising a compound having a structure of Formula I can further comprise an additional therapeutic agent selected form the group consisting of enzalutamide, Galeterone, ARN-509; abiraterone, bicalutamide, nilutamide, flutamide, cyproterone acetate, docetaxel, Bevacizumab (Avastin), OSU-HDAC42, VITAXIN, sunitumib, ZD-4054, Cabazitaxel (XRP-6258), MDX-010 (Ipilimumab), OGX 427, OGX 011, finasteride, dutasteride, turosteride, bexlosteride, izonsteride, FCE 28260, SKF105,111, ODM-201, radium 233, or related compounds thereof.

In some embodiments, compounds of Formula I which result in unstable structures and/or unsatisfied valences are not included within the scope of the invention.

In another embodiment, the present disclosure provides a pharmaceutical composition comprising any of the foregoing compounds of Formula I and a pharmaceutically acceptable carrier.

Compounds as described herein may be in the free form or in the form of a salt thereof. In some embodiments, compounds as described herein may be in the form of a pharmaceutically acceptable salt, which are known in the art (Berge et al., *J. Pharm. Sci.* 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

III. Methods

The present compounds find use in any number of methods. For example, in some embodiments the compounds can be useful in methods for modulating androgen receptor (AR). Accordingly, in one embodiment, the present disclosure provides the use of any one of the foregoing compounds of Formula I for modulating androgen receptor (AR) activity. For example in some embodiments, modulating androgen receptor (AR) activity can be in a mammalian cell. Modulating androgen receptor (AR) may be in a subject in need thereof (e.g., a mammalian subject) and for treatment of any of the described conditions or diseases.

In other embodiments, modulating androgen receptor (AR) activity can be for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, age related macular degeneration, and combinations thereof. For example in some embodiments, the indication is prostate cancer. In other embodiments, the prostate cancer is castration resistant prostate cancer (also referred to as hormone refractory, androgen-independent, androgen deprivation resistant, androgen ablation resistant, androgen depletion-independent, castration-recurrent, anti-androgen-recurrent). While in other embodiments, the prostate cancer is androgen dependent prostate cancer. In other embodiments, the spinal and bulbar muscular atrophy is Kennedy's disease.

In some embodiments, compounds as described herein may be administered to a subject. In one embodiment, the present invention can be directed to a method of treating castration resistant prostate cancer comprising administering a pharmaceutical composition comprising a compound having a structure of Formula I. In some embodiments, the present invention can be directed to a method of treating androgen-dependent prostate cancer comprising administering a pharmaceutical composition comprising a compound having a structure of Formula I. In other embodiments, the present invention can be directed to a method of treating androgen-independent prostate cancer comprising administering a pharmaceutical composition comprising a compound having a structure of Formula I.

In other embodiments, the present disclosure provides a method of modulating androgen receptor (AR) activity, the method comprising administering any one of the foregoing compounds of Formula I, pharmaceutically acceptable salt thereof, or pharmaceutical composition of Formula I as described herein (including compositions comprising a compound of Formula I and an additional therapeutic agent), to a subject (e.g., mammal) in need thereof. In some embodiments, modulating androgen receptor (AR) activity can be in a mammalian cell. In other embodiments, modulating androgen receptor (AR) activity can be in a mammal. In one embodiment, modulating androgen receptor (AR) activity can be in a human.

The modulating androgen receptor (AR) activity may be for inhibiting AR N-terminal domain activity. The modulating androgen receptor (AR) activity may be for inhibiting androgen receptor (AR) activity. The modulating may be in vivo. The modulating androgen receptor (AR) activity may be for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy (e.g., Kennedy's disease), and age related macular degeneration. The indication may be prostate cancer. The prostate cancer may be castration-resistant prostate cancer. The prostate cancer may be androgen dependent prostate cancer.

In accordance with another embodiment, there is provided a use of the compounds of Formula I, pharmaceutically acceptable salt thereof, or pharmaceutical composition of Formula I as described herein for preparation of a medicament for modulating androgen receptor (AR).

Alternatively, in one embodiment, the method of modulating androgen receptor activity, comprising administering Formula I, pharmaceutically acceptable salt thereof, or pharmaceutical composition of Formula I as described herein, are provided. In some embodiments, the administration may be to a mammal. In other embodiments, the administering may be to a mammal in need thereof and in an effective amount for the treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy (e.g., Kennedy's disease), age related macular degeneration, and combinations thereof.

Androgen ablation therapy causes a temporary reduction in prostate cancer tumor burden, but the malignancy will begin to grow again in the absence of testicular androgens to form castrate resistant prostate cancer (CRPC). A rising titer of serum prostate-specific antigen (PSA) after androgen ablation therapy indicates biochemical failure, the emergence of CRPC, and re-initiation of an androgen receptor (AR) transcription program. Most patients succumb to CRPC within two years of biochemical failure.

AR is a transcription factor and a validated target for prostate cancer therapy. Current therapies include androgen ablation and administration of antiandrogens. Most CRPC is suspected to be AR-dependent. AR has distinct functional domains that include the C-terminus ligand-binding domain (LBD), a DNA-binding domain (DBD), and an amino-terminal domain (NTD). AR NTD contains the activation function-1 (AF-1) that contributes most of the activity to the AR. Recently, splice variants of the AR that lack the LBD have been reported in prostate cancer cell lines (VCaP and 22Rv1), and in CRPC tissues. To date more than 20 splice variants of AR have been detected. Splice variants V7 and V567es are clinically relevant with levels of expression correlated to poor survival and CRPC. AR V567es is solely expressed in 20% of metastases. Abiraterone resistance is associated with expression of AR splice variants. Enzalutamide also increases levels of expression of these constitutively active AR splice variants. These splice variants lack LBD and thereby would not be inhibited by current therapies that target the AR LBD such as antiandrogens or androgen ablation therapy. A single patient with advanced prostate cancer can have many lesions throughout the body and skeleton and each tumor can have differing levels of expression of AR.

In some embodiments, the compounds as described herein or pharmaceutically acceptable salts thereof can find use in the diagnostic of at least one indication selected from the group consisting of: prostate cancer, breast cancer, ovarian cancer, endometrial cancer, salivary gland carcinoma, benign prostatic hyperplasia, hair loss, acne, hirsutism, ovarian cysts, polycystic ovary disease, precocious puberty, spinal and bulbar muscular atrophy, and age-related macular degeneration. In some embodiments, the compounds as described herein or acceptable salts thereof above can be used in the preparation of a medicament or a composition for imaging the prostate, for example for imaging benign prostate conditions or for imaging prostate cancer in a subject in need of such imaging (for example for diagnosis and/or location of prostate tumors).

In some embodiments, pharmaceutical compositions useful in modulating androgen receptor (AR) activity, in accordance with this invention may comprise a salt of such a compound, preferably a pharmaceutically or physiologically acceptable salt. Pharmaceutical preparations can typically comprise one or more carriers, excipients or diluents acceptable for the mode of administration of the preparation, be it by injection, inhalation, topical administration, lavage, or other modes suitable for the selected treatment. Suitable carriers, excipients or diluents are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in Remington: the Science & Practice of Pharmacy by Alfonso Gennaro, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

In another aspect, the present disclosure provides a pharmaceutical composition comprising a compound as described herein, and an additional therapeutic agent and/or a pharmaceutically acceptable carrier. In some embodiments, the additional therapeutic agent can be for treating prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy or age related macular degeneration. In other embodiments, the additional therapeutic agent can be enzalutamide, galeterone, ARN-509, ODN-201 abiraterone, bicalutamide, nilutamide, flutamide, cyproterone acetate, docetaxel, Bevacizumab (Avastin), OSU-HDAC42, VITAXIN, sunitumib, ZD-4054, Cabazitaxel (XRP-6258), MDX-010 (Ipilimumab), OGX 427, OGX 011, finasteride, dutasteride, turosteride, bexlosteride, izonsteride, FCE 28260, SKF105,111 ODM-201, or related compounds thereof.

Compounds described herein may also be used in assays and for research purposes. Definitions used include ligand dependent activation of the androgen receptor (AR) by androgens such as dihydrotestosterone (DHT) or the synthetic androgen (R1881) used for research purposes. Ligand-independent activation of the androgen receptor (AR) refers to transactivation of the full length androgen receptor (AR) in the absence of androgen (ligand) by, for example, stimulation of the cAMP dependent protein kinase (PKA) pathway with forskolin (FSK). Some compounds and compositions of this invention may inhibit both FSK and androgen (e.g. R1881, a synthetic androgen) induction of ARE luciferase (ARE-luc). Constitutive activity of the androgen receptor (AR) refers to splice variants lacking the androgen receptor (AR) ligand-binding domain. Such compounds may block a mechanism that is common to both ligand dependent and ligand independent activation of the androgen receptor (AR), as well as constitutively active splice variants of the androgen receptor (AR) that lack ligand-binding domain. This could involve any step in activation of the androgen receptor (AR) including dissociation of heatshock proteins, essential posttranslational modifications (e.g., acetylation, phosphorylation), nuclear translocation, protein-protein interactions, formation of the transcriptional complex, release of co repressors, and/or increased degradation. Some compounds and compositions of this invention may inhibit ligand-only activity and may interfere with a mechanism specific to ligand dependent activation (e.g., accessibility of the ligand binding domain (LBD) to androgen). Numerous disorders in addition to prostate cancer involve the androgen axis (e.g., acne, hirsutism, alopecia, benign prostatic hyperplasia) and compounds interfering with this mechanism may be used to treat such conditions. Some compounds and compositions of this invention may only inhibit FSK induction and may be specific inhibitors to ligand independent activation of the androgen receptor (AR). These compounds and compositions may interfere with the cascade of events that normally occur with FSK and/or PKA activity or any downstream effects that may play a role on the androgen receptor (AR) (e.g. FSK increases MAPK activity which has a potent effect on androgen receptor (AR) activity). Examples may include an inhibitor of cAMP and or PKA or other kinases. Some compounds and compositions of this invention may induce basal levels of activity of the AR (no androgen or stimulation of the PKA pathway). Some compounds and compositions of this invention may increase induction by R1881 or FSK. Such compounds and compositions may stimulate transcription or transactivation of the AR. Some compounds and compositions of this invention may inhibit activity of the androgen receptor. Interleukin 6 (IL 6) also causes ligand independent activation of the androgen receptor (AR) in LNCaP cells and can be used in addition to FSK.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

It is to be noted that dosage values may vary with the exact imaging protocol. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens can be adjusted to provide the optimum imaging result. For example, a single bolus can be administered, several divided doses can be administered over time or the dose can be proportionally reduced or increased as indicated by the imaging results. It can be advantageous to formulate parenteral compositions in dosage unit form for ease of administration and uniformity of dosage.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances, such as in severe disease conditions, substantial excesses of the compositions may be administered for therapeutic effects. Some compounds of this invention may be toxic at some concentrations. Titration studies may be used to determine toxic and non-toxic concentrations. Toxicity may be evaluated by examining a particular compound's or composition's specificity across cell lines using PC3 or DU145 cells as possible negative controls since these cells do not express functional AR. Animal studies may be used to provide an indication if the compound has any effects on other tissues. Systemic therapy that targets the AR will not likely cause major problems to other tissues since antiandrogens and androgen insensitivity syndrome are not fatal.

Compounds for use in the present invention may be obtained from medical sources or modified using known methodologies from naturally occurring compounds. In addition, methods of preparing or synthesizing compounds of the present invention will be understood by a person of skill in the art having reference to known chemical synthesis principles. For example, Auzou et al 1974 *European Journal of Medicinal Chemistry* 9(5), 548-554 describes suitable synthetic procedures that may be considered and suitably adapted for preparing compounds of any one of the compounds of structure (I) as set out above. Other references that may be helpful include: Debasish Das, Jyh-Fu Lee and Soofin Cheng "Sulfonic acid functionalized mesoporous MCM-41 silica as a convenient catalyst for Bisphenol-A synthesis" *Chemical Communications*, (2001) 2178-2179; U.S. Pat. No. 2,571,217 Davis, Orris L.; Knight, Horace S.; Skinner, John R. (Shell Development Co.) "Halohydrin ethers of phenols." (1951); and Rokicki, G.; Pawlicki, J.; Kuran, W. "Reactions of 4-chloromethyl-1,3-dioxolan-2-one with phenols as a new route to polyols and cyclic carbonates." Journal fuer Praktische Chemie (Leipzig) (1985) 327, 718-722.

In some embodiments, compounds and all different forms thereof as described herein may be used, for example, and without limitation, in combination with other treatment methods for at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age related macular degeneration. For example, compounds and all their different forms as described herein may be used as neoadjuvant (prior), adjunctive (during), and/or adjuvant (after) therapy with surgery, radiation (brachytherapy or external beam), or other therapies (eg. HIFU), and in combination with chemotherapies, androgen ablation, antiandrogens or any other therapeutic approach.

In an exemplary embodiment for imaging the prostate, a dose of the disclosed compounds in solution (typically 5 to 10 millicuries or 200 to 400 MBq) can be typically injected rapidly into a saline drip running into a vein, in a patient. Then, the patient is placed in the SPECT for a series of one or more scans which may take from 20 minutes to as long as an hour (often, only about one quarter of the body length may be imaged at a time). Methods for SPECT scanning are well known in the art.

The compounds described herein may be used for in vivo or in vitro research uses (i.e. non-clinical) to investigate the mechanisms of orphan and nuclear receptors (including steroid receptors such as androgen receptor (AR)). Furthermore, these compounds may be used individually or as part of a kit for in vivo or in vitro research to investigate signal transduction pathways and/or the activation of orphan and nuclear receptors using recombinant proteins, cells maintained in culture, and/or animal models.

EXAMPLES

All non-aqueous reactions were performed in flame-dried round bottomed flasks. The flasks were fitted with rubber septa and reactions were conducted under a positive pressure of argon unless otherwise specified. Stainless steel syringes were used to transfer air- and moisture-sensitive liquids. Flash column chromatography was performed as described by Still et al. (Still, W. C.; Kahn, M.; Mitra, A. *J. Org. Chem.* 1978, 43, 2923) using 230-400 mesh silica gel. Thin-layer chromatography was performed using aluminum plates pre-coated with 0.25 mm 230-400 mesh silica gel impregnated with a fluorescent indicator (254 nm). Thin-layer chromatography plates were visualized by exposure to ultraviolet light and a "Seebach" staining solution (700 mL water, 10.5 g Cerium (IV) sulphate tetrahydrate, 15.0 g molybdato phosphoric acid, 17.5 g sulphuric acid) followed by heating (~1 min) with a heating gun (~250° C.). Organic solutions were concentrated on Büchi R-114 rotatory evaporators at reduced pressure (15-30 torr, house vacuum) at 25-40° C.

Commercial regents and solvents were used as received. All solvents used for extraction and chromatography were HPLC grade. Normal-phase Si gel Sep paks™ were purchased from waters, Inc. Thin-layer chromatography plates were Kieselgel 60F$_{254}$. All synthetic reagents were purchased from Sigma Aldrich and Fisher Scientific Canada.

Example 1

Synthesis of (R)-3-(4-(2-(4-((R)-2-chloro-3-hydroxypropoxy)phenyl)propan-2-yl)phenoxy)propane-1,2-diol (1a)

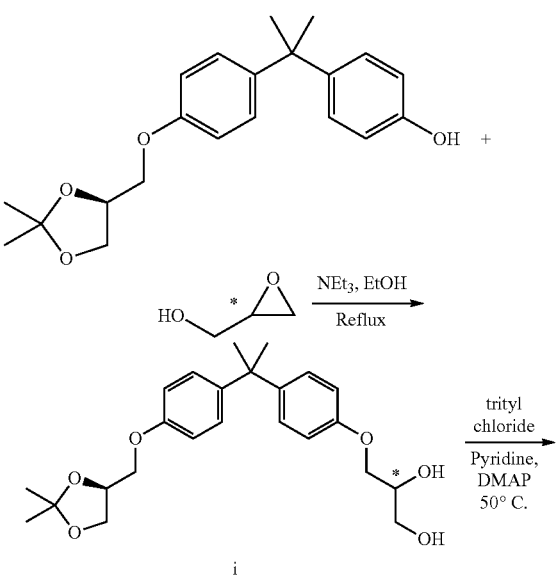

i

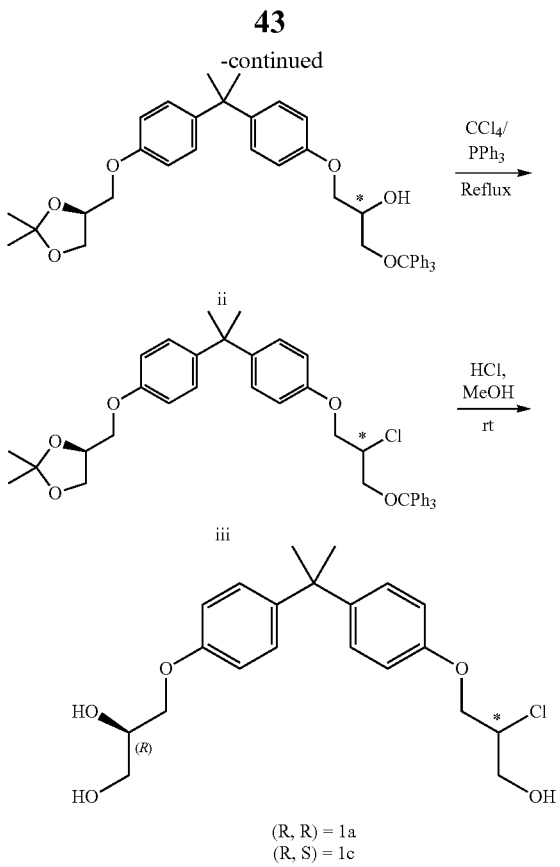

(R, R) = 1a
(R, S) = 1c

Compound i

Figure 4A:
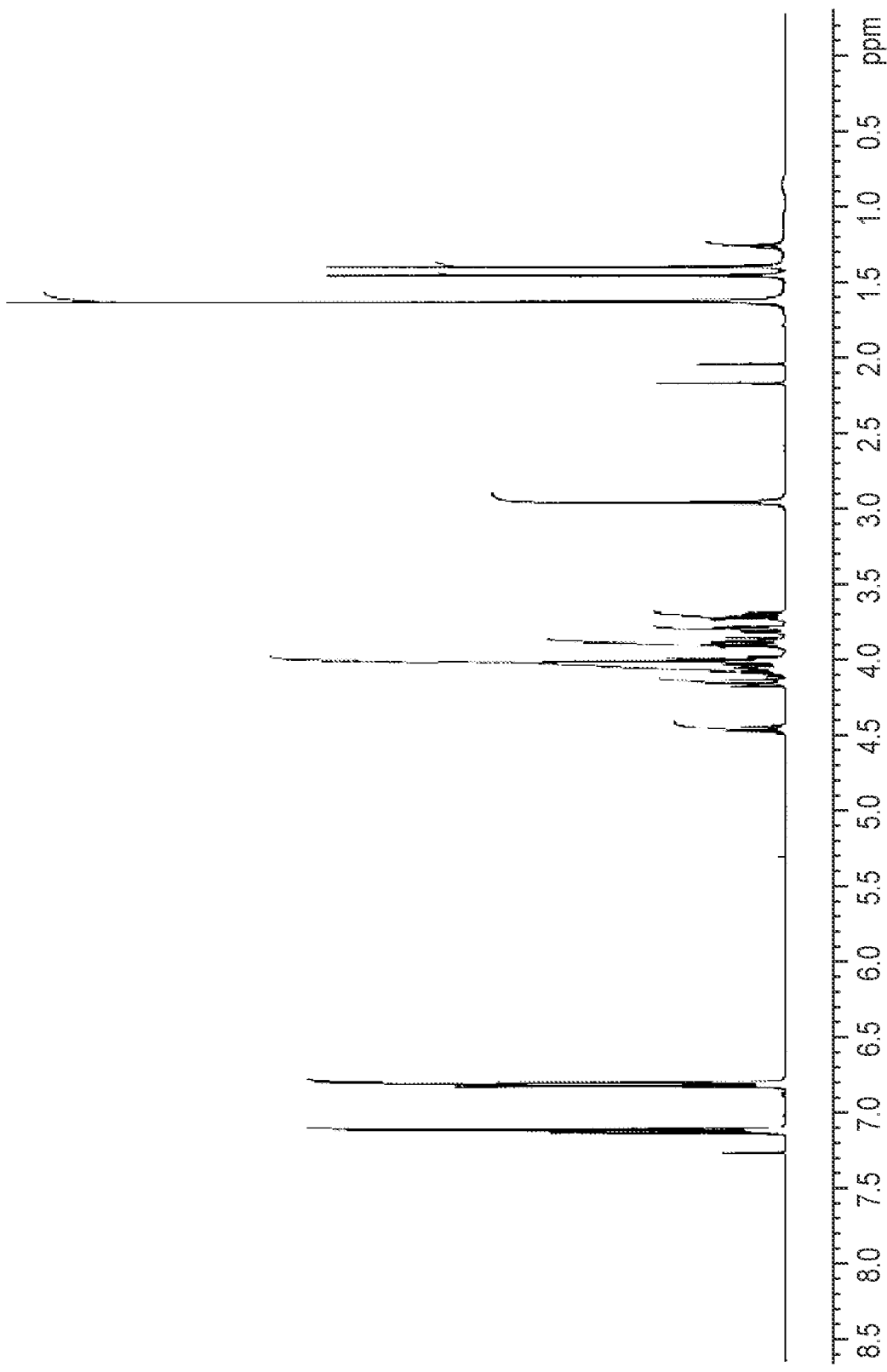
FIGS. 4A and 4B shows the $^1$H NMR and the $^{13}$C NMR spectra for (R)-3-(4-(2-(4-(((S)-2,2-dimethyl -1,3-dioxolan-4-yl)methoxy)phenyl)propan-2-yl)phenoxy)propane-1,2-diol, respectively.
Figure 4B:
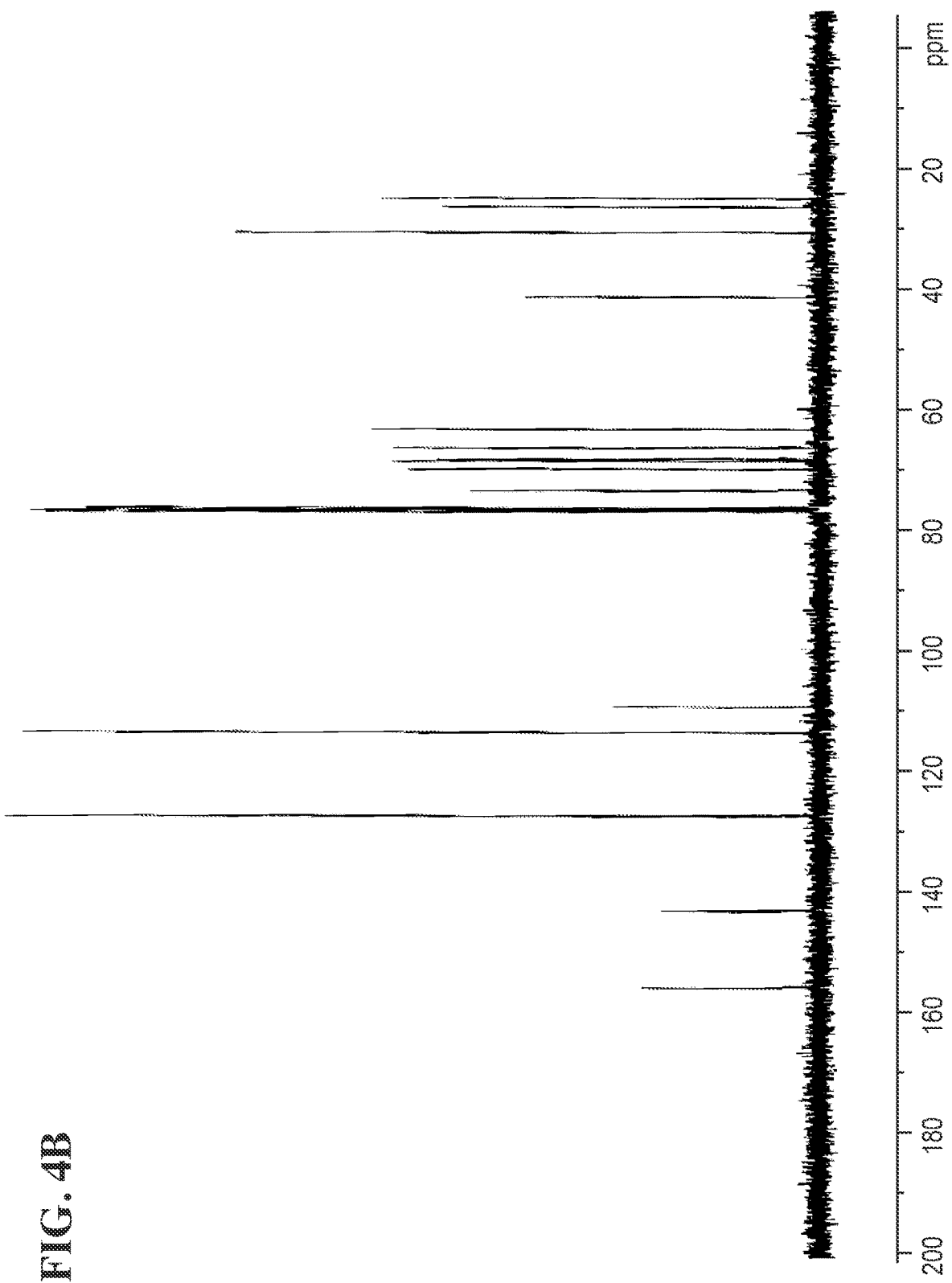

To a stirred solution of (S)-4-(2-(4-((2,2-dimethyl-1,3-dioxolan-4-yl)methoxy)phenyl)propan-2-yl)phenol (1 equiv) in ethanol at rt was added NEt₃ (1 equiv) and (S)-oxiran-2-ylmethanol (3 equiv), then the reaction mixture was refluxed. After the completion of the reaction, the product was extracted with ethyl acetate (×3). The organic layer was washed with deionized water, dried over anhydrous magnesium sulfate, filtered, and concentrated under reduced pressure. The resulting residue was purified by flash column chromatography on silica gel to provide (R)-3-(4-(2-(4-(((S)-2,2-dimethyl-1,3-dioxolan-4-yl)methoxy)phenyl)propan-2-yl)phenoxy)propane-1,2-diol. See FIGS. 4A-4B for NMR spectra.

Compound ii

Figure 3A:
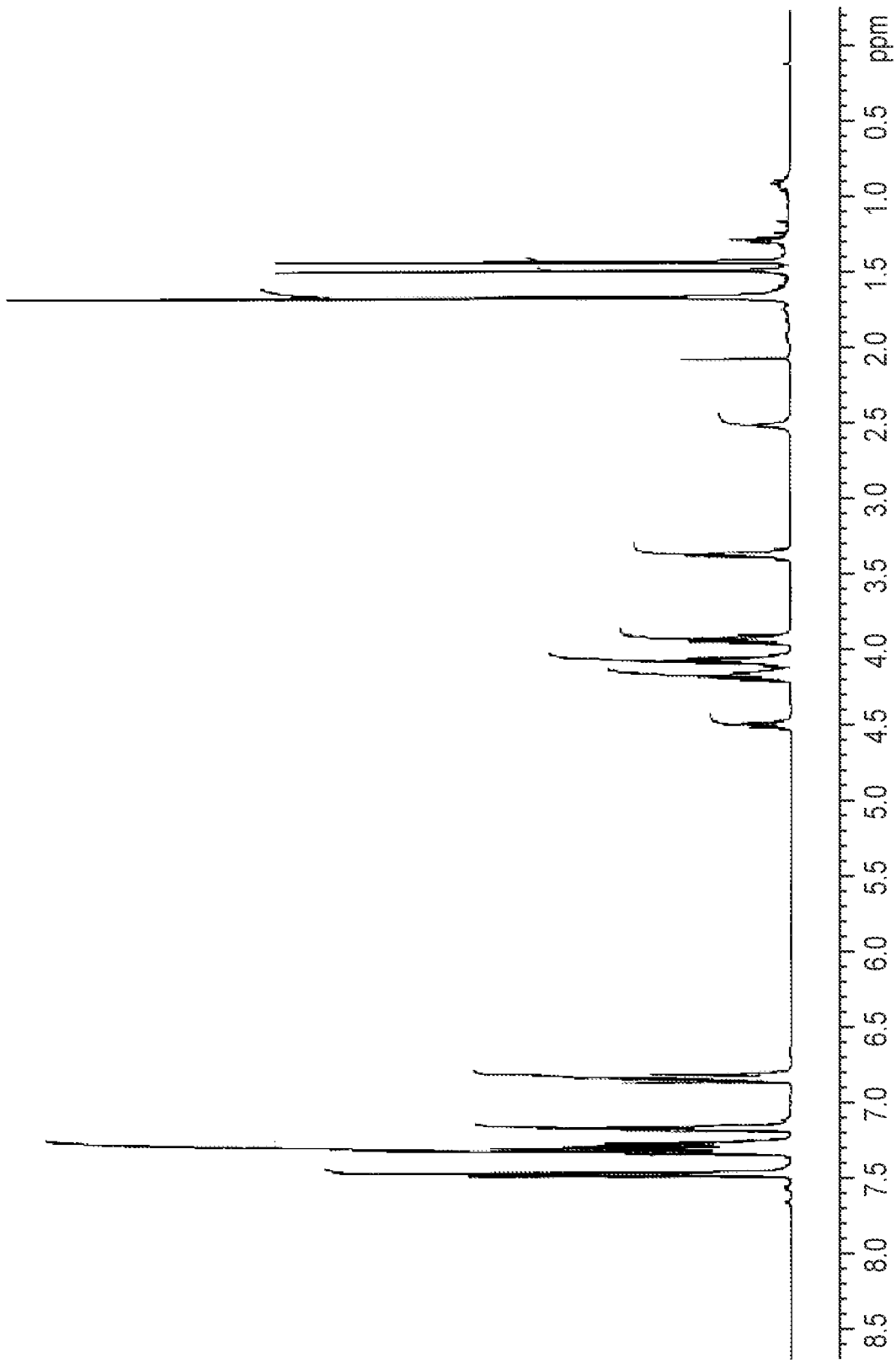
FIGS. 3A and 3B shows the $^1$H NMR and the $^{13}$C NMR spectra for (S)-1-(4-(2-(4-(((S)-2,2-dimethyl-1,3-dioxolan-4-yl)methoxy)phenyl)propan-2-yl)phenoxy)-3-(triphenyl-14-oxidanyl)propan-2-ol, respectively.
Figure 3B:
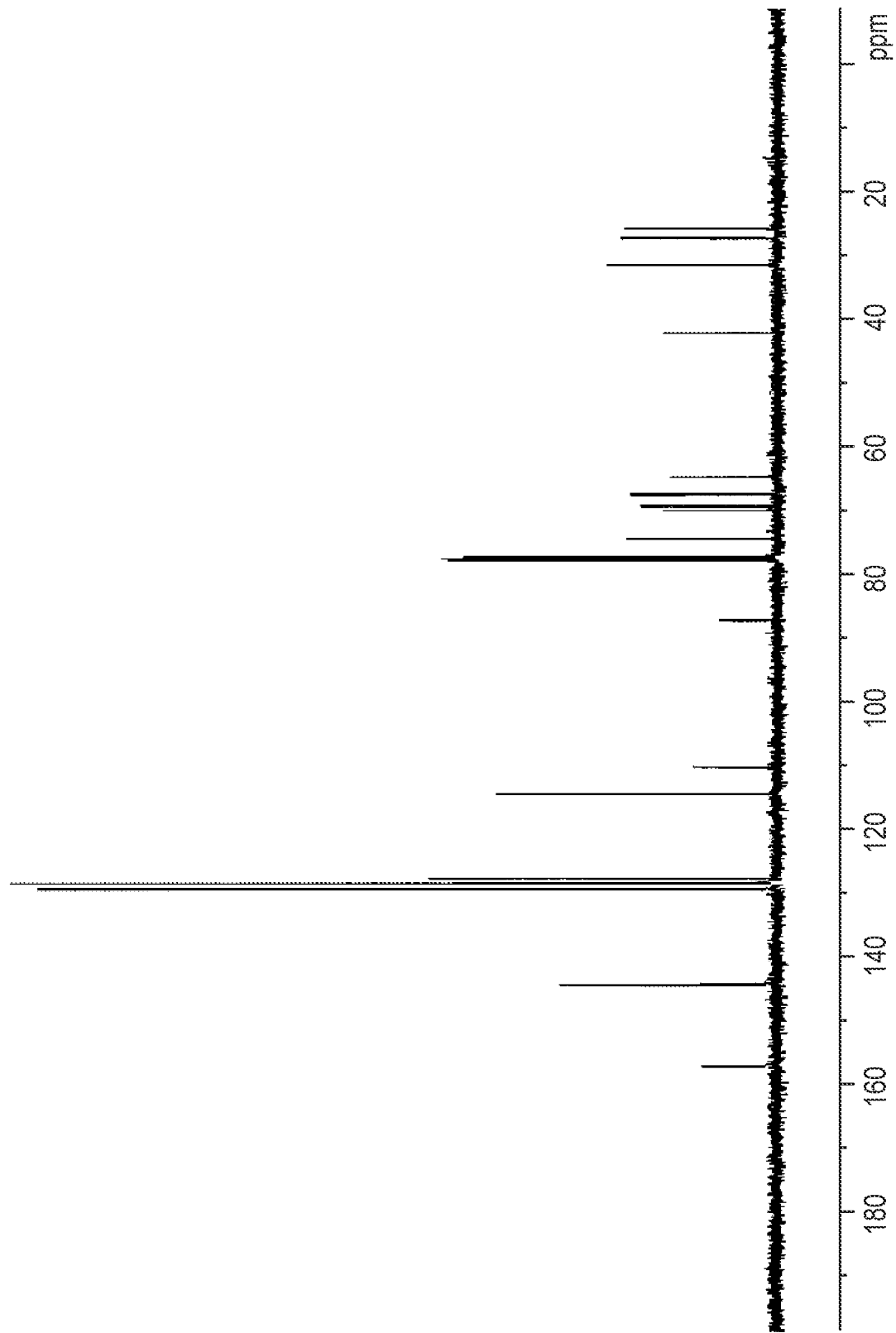

To a mixture of (R)-3-(4-(2-(4-(((S)-2,2-dimethyl-1,3-dioxolan-4-yl)methoxy)phenyl)propan-2-yl)phenoxy)propane-1,2-diol (1 equiv) and trityl chloride, pyridine and DMAP were added. The reaction mixture was heated to 50° C. After the completion of the reaction, the product was extracted with ethyl acetate (×3). The organic layer was washed with deionized water, dried over anhydrous magnesium sulfate, filtered, and concentrated under reduced pressure. The resulting residue was purified by flash column chromatography on silica gel to provide (S)-1-(4-(2-(4-(((S)-2,2-dimethyl-1,3-dioxolan-4-yl)methoxy)phenyl)propan-2-yl)phenoxy)-3-(triphenyl-14-oxidanyl)propan-2-ol. See FIGS. 3A-3B for NMR spectra.

Compound iii

Figure 2:
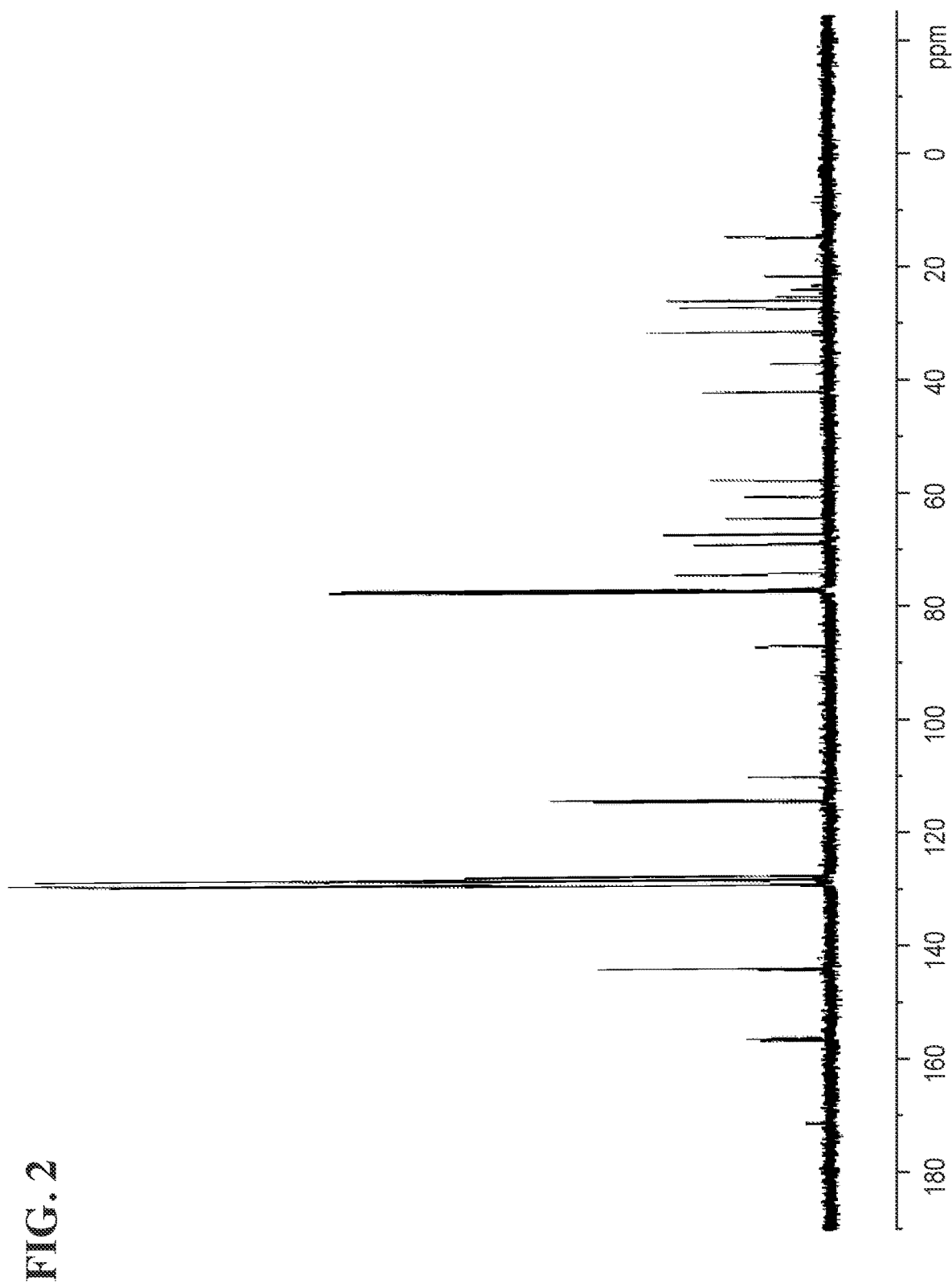
FIG. 2 shows the $^{13}$C NMR spectrum for (S)-4-((4-(2-(4-((S)-2-chloro-3-(triphenyl-14-oxidanyl)propoxy)phenyl) propan-2-yl)phenoxy)methyl)-2,2-dimethyl-1,3-dioxolane.

To a solution of (S)-1-(4-(2-(4-(((S)-2,2-dimethyl-1,3-dioxolan-4-yl)methoxy)phenyl)phenoxy)-3-(triphenyl-14-oxidanyl)propan-2-ol (1 equiv) in carbon tetrachloride, PPh₃ was added and the reaction mixture was refluxed. After the completion of the reaction, the product was extracted with ethyl acetate (×3). The organic layer was washed with deionized water, dried over anhydrous magnesium sulfate, filtered, and concentrated under reduced pressure. The resulting residue was purified by flash column chromatography on silica gel to provide (S)-4-((4-(2-(4-((S)-2-chloro-3-(triphenyl-14-oxidanyl)propoxy)phenyl)propan-2-yl)phenoxy)methyl)-2,2-dimethyl-1,3-dioxolane. See FIG. 2 for NMR spectrum.

Compound 1a

Figure 1B:
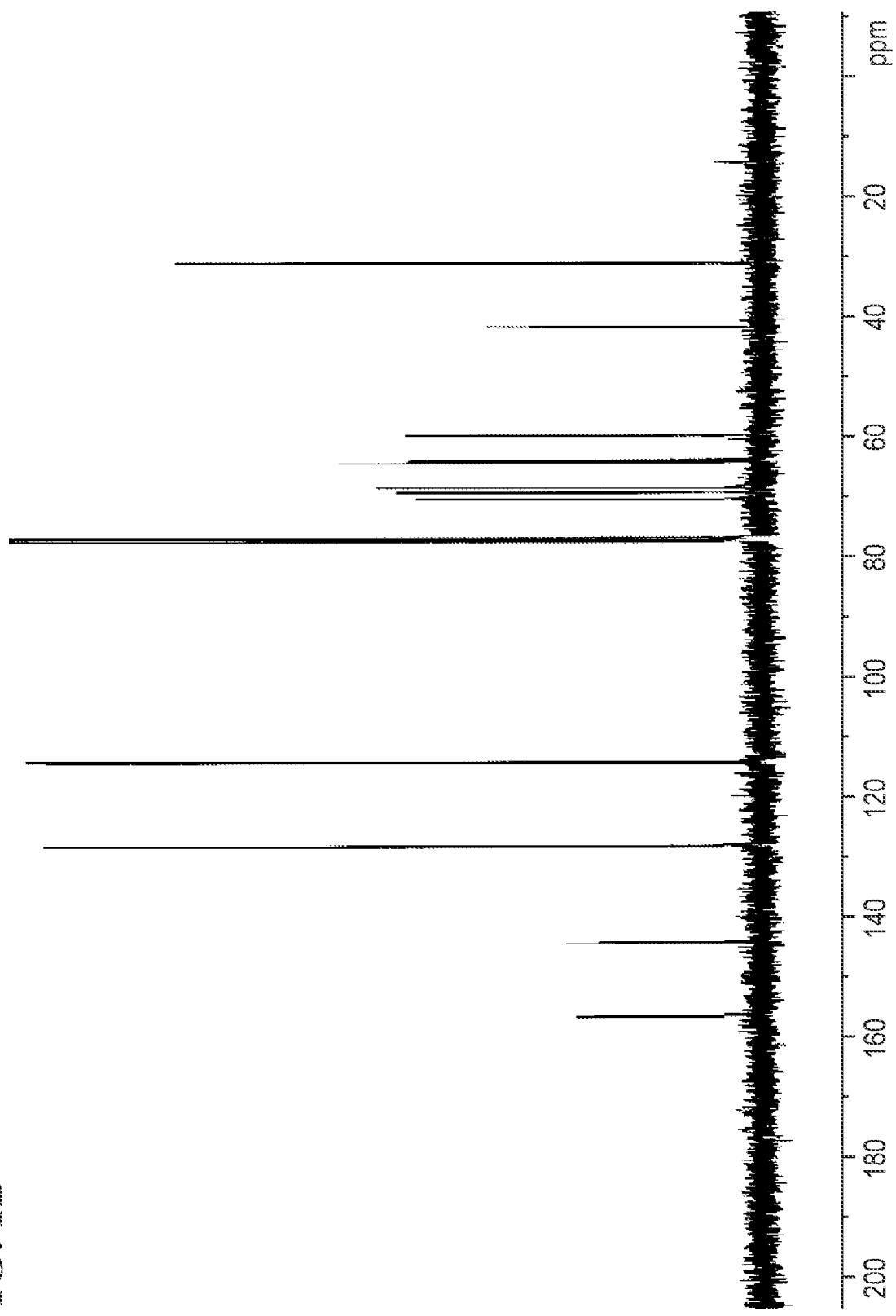

To a solution of (S)-4-((4-(2-(4-((S)-2-chloro-3-(triphenyl-14-oxidanyl)propoxy)phenyl)propan-2-yl)phenoxy)methyl)-2,2-dimethyl-1,3-dioxolane (1 equiv) in methanol, HCl was added and the reaction was stirred at rt. After the completion of the reaction, the product was extracted with ethyl acetate (×3). The organic layer was washed with deionized water, dried over anhydrous magnesium sulfate, filtered, and concentrated under reduced pressure. The resulting residue was purified by flash column chromatography on silica gel to provide Compound 1a. See FIG. 1A-1B for NMR spectra of Compound 1a.

Example 2

Synthesis of (R)-3-(4-(2-(4-((S)-2-chloro-3-hydroxypropdxy)phenyl)propan-2-yl)phenoxy)propane-1,2-diol (1c)

Compound (1c)

Figure 5A:
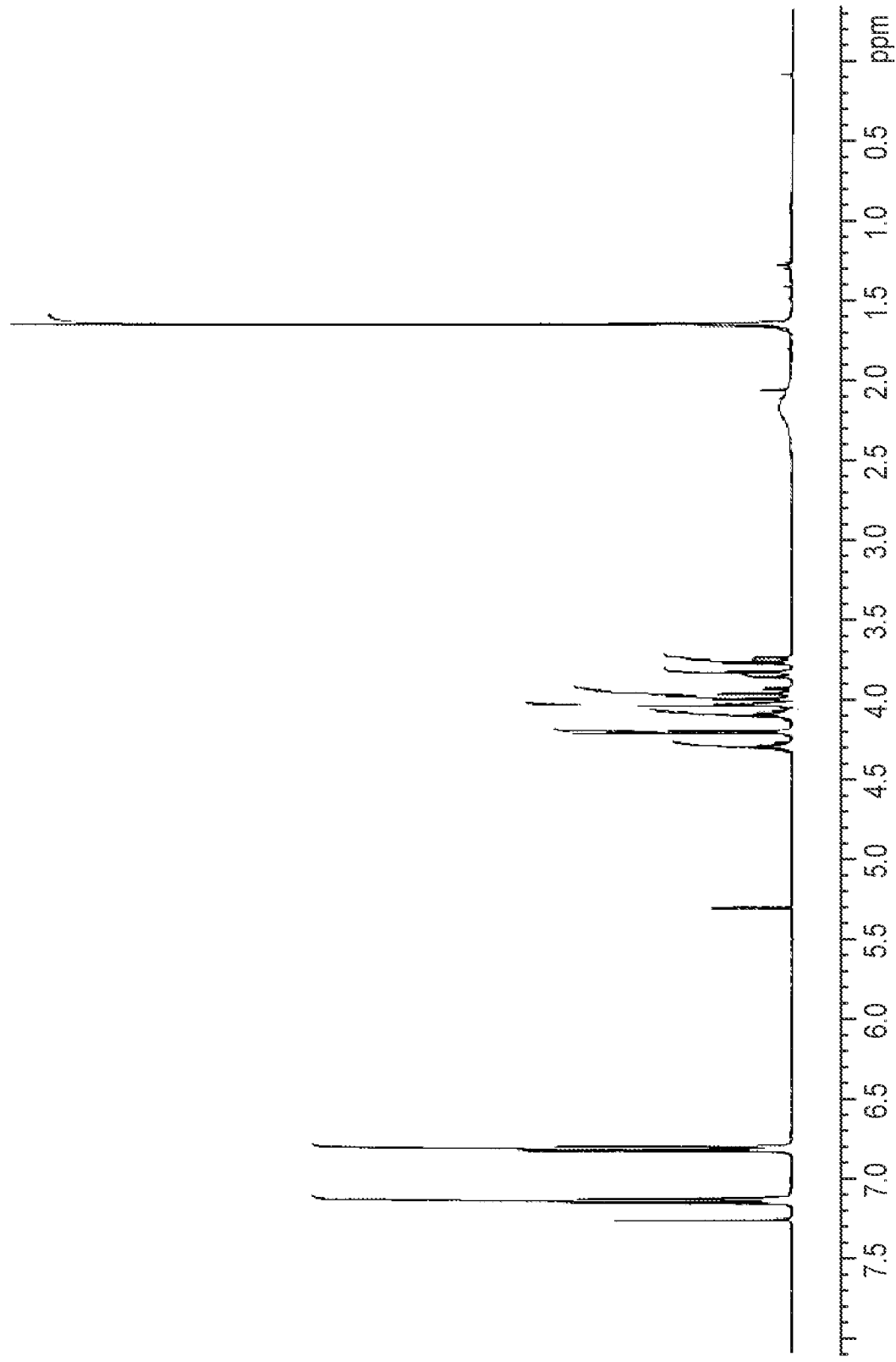
FIGS. 5A and 5B shows the $^1$H NMR and the $^{13}$C NMR spectra for Compound 1c, respectively.
Figure 5B:
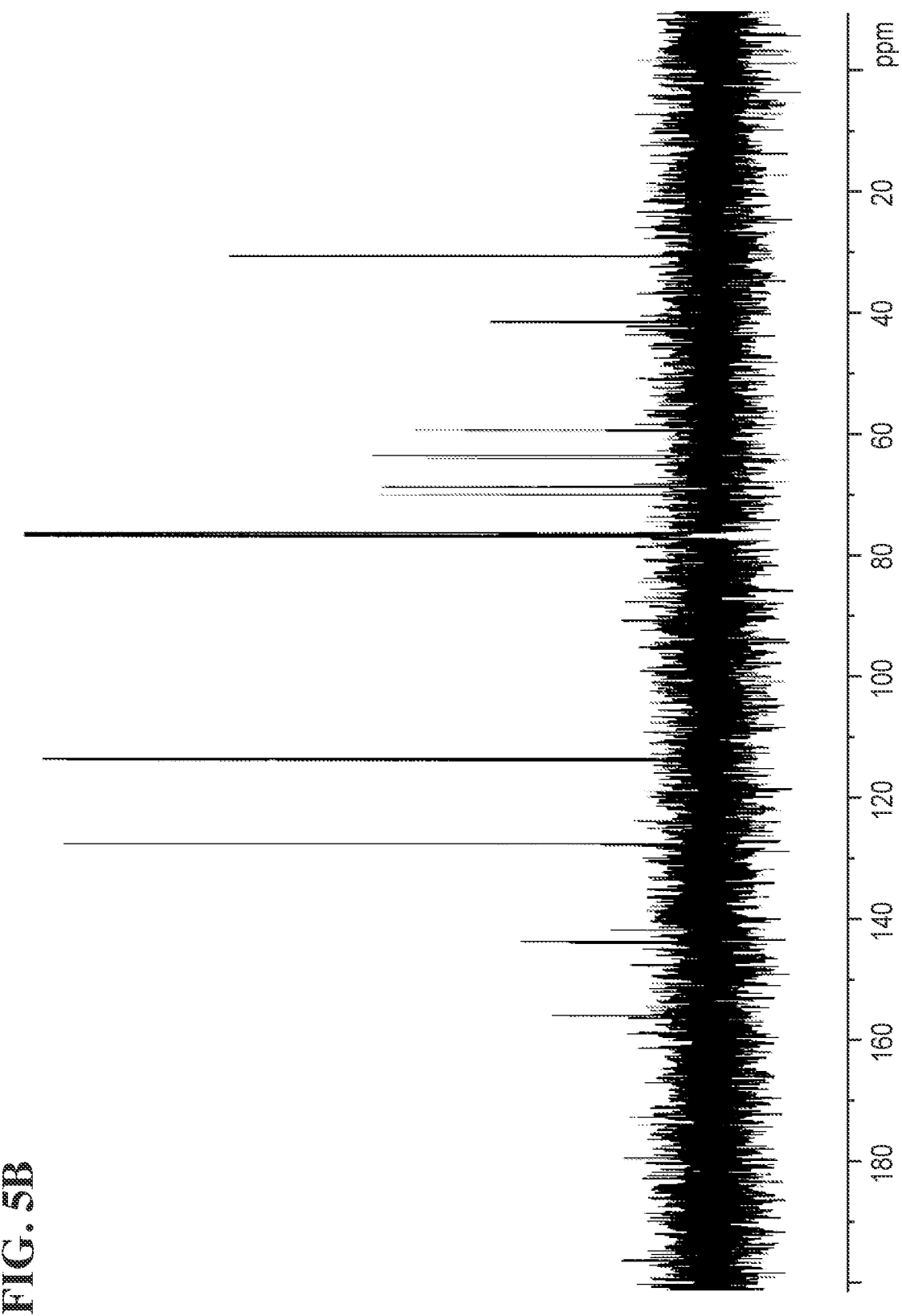

Compound 1c was synthesized according to Example 1 but starting with (R)-oxiran-2-ylmethanol instead of (S)-oxiran-2ylmethanol. See FIG. 5A-5B for NMR spectra of Compound1c.

Example 3

Compound Activity

LNCaP cells were transiently transfected with PSA (6.1 kb)-luciferase for 24 h prior to pre-treatment with compounds of the invention (e.g., Compound 1c) ranging in concentration from 62.5 ng/ml to 1.5 ug/ml for 1 hour before the addition of vehicle, or synthetic androgen, R1881 (1 nM) to induce luciferase production. After 24 h of incubation with R1881, the cells were harvested, and relative luciferase activities were determined. To determine the IC₅₀, treatments were normalized to the predicted maximal activity induction (in the absence of test compounds, vehicle only).

TABLE 2

$IC_{50}$ values for selected compounds (μM)

| Compound | Trial 1 | Trial 2 | Trial 3 | Trial 4 | Average $IC_{50}$ |
|---|---|---|---|---|---|
| 1c | 14.01 | 19.38 | 17.00 | 15.83 | 16.69 ± 2.68 |

One skilled in the art will recognize that variations to the order of the steps and reagents discussed in the Examples are possible.

In addition, protecting group strategies may be employed for preparation of the compounds disclosed herein. Such strategies are well known to those of skill in the art.

Exemplary protecting groups and related strategies are disclosed in Greene's Protective Groups in Organic Synthesis, Wiley-Interscience; 4 edition (Oct. 30, 2006), which is hereby incorporated by reference in its entirety. In certain embodiments, a protecting group is used to mask an alcohol moiety while performing other chemical transformations. After removal of the protecting group, the free hydroxyl is obtained. Such protecting groups and strategies are well known in the art.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method for modulating androgen receptor activity, comprising:
administering to a patient in need thereof a compound having the following structure (I):

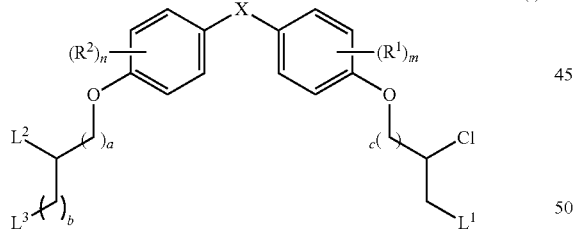

(I)

or a pharmaceutically acceptable salt, tautomer or stereoisomer thereof, wherein:
wherein:
X is —C($R^3R^4$)—;
$R^1$ and $R^2$ are each independently H, halogen, $C_1$-$C_{10}$ alkyl, $C_2$-$C_{10}$ alkenyl, $C_2$-$C_{10}$ alkynyl, —OH, —O$R^5$, —O($C_1$-$C_6$)alkyl, —OC(=O)$R^{13}$, $C_1$-$C_{10}$ acyl, —S(O)$_{0-2}R^5$, —NO$_2$, —CN, —NH$_2$, —NH$R^5$, —N($R^5R^6$), —CO$_2$H, CO$_2R^{14}$, or CONR$^5R^6$;
$R^3$ and $R^4$ are each independently H, $C_1$-$C_{10}$ alkyl, $C_2$-$C_{10}$ alkenyl, or $C_2$-$C_{10}$ alkynyl;
$R^5$ and $R^6$ are each independently H, $C_1$-$C_{10}$ alkyl, $C_2$-$C_{10}$ alkenyl, or $C_2$-$C_{10}$ alkynyl;
$R^7$ is each independently H, $C_1$-$C_{10}$ alkyl, $C_2$-$C_{10}$ alkenyl, $C_2$-$C_{10}$ alkynyl, aryl, aminocarbonyl, $C_1$-$C_{10}$ alkylcarbonyl, $C_2$-$C_{10}$ alkenylcarbonyl, $C_2$-$C_{10}$ alkynylcarbonyl, alkylaminocarbonyl, $C_2$-$C_{10}$ alkenylaminocarbonyl, or $C_2$-$C_{10}$ alkynylaminocarbonyl;

$R^{13}$ is each independently $C_1$-$C_{10}$ alkyl, $C_2$-$C_{10}$ alkenyl, or $C_2$-$C_{10}$ alkynyl;

$R^{14}$ is each independently H, $C_1$-$C_{10}$ alkyl, $C_2$-$C_{10}$ alkenyl, $C_2$-$C_{10}$ alkynyl, or aryl;

$L^1$ is hydroxyl or —OC(=O)$R^{13}$;

$L^2$ and $L^3$ are each independently H, halogen, hydroxyl, —OC(=O)$R^{13}$, —O$C_1$-$C_{10}$ alkyl, —O$C_2$-$C_{10}$ alkenyl, —O$C_2$-$C_{10}$ alkynyl, —O$R^{15}$, —S$R^5$, —N$R^5R^6$, —O($C_1$-$C_{10}$ acyl), —O$C_1$-$C_{10}$ alkylene-(—O—$C_1$-$C_{10}$ alkyl)$_p$, —O$C_1$-$C_{10}$ alkylene-(—O—$C_2$-$C_{10}$ alkynyl)$_p$, —O$C_1$-$C_{10}$ alkylene-(—O—$C_2$-$C_{10}$ alkenyl)$_p$, —O$C_2$-$C_{10}$ alkenylene-(—O—$C_1$-$C_{10}$ alkyl)$_p$, —O$C_2$-$C_{10}$ alkenylene-(—O—$C_2$-$C_{10}$ alkenyl)$_p$, —O$C_2$-$C_{10}$ alkenylene-(—O—$C_2$-$C_{10}$ alkynyl)$_p$, —O$C_2$-$C_{10}$ alkynylene-(—O—$C_1$-$C_{10}$ alkyl)$_p$, —O$C_2$-$C_{10}$ alkynylene-(—O—$C_1$-$C_{10}$ alkenyl)$_p$, —O$C_2$-$C_{10}$ alkynylene-(—O—$C_2$-$C_{10}$ alkynyl)$_p$, carbocyclyl, aryl, heterocyclyl, or heteroaryl;

wherein at least one of $L^2$ and $L^3$ is a hydroxyl, —OC(=O)$R^{13}$, substituted or unsubstituted carbocyclyl, substituted or unsubstituted aryl, substituted or unsubstituted heterocyclyl, or substituted or unsubstituted heteroaryl;

$R^{15}$ is each independently selected from the group consisting of

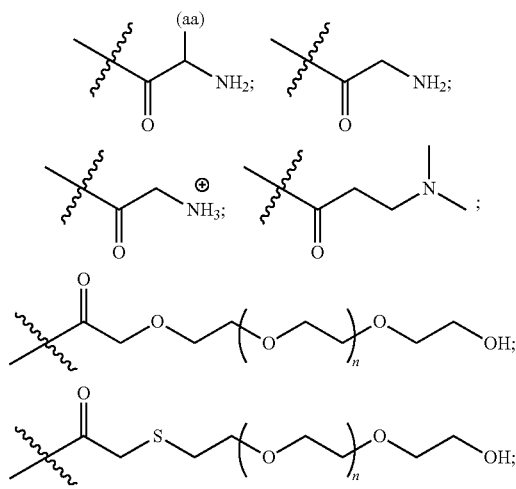

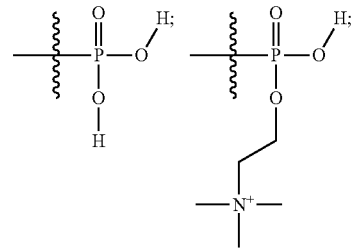

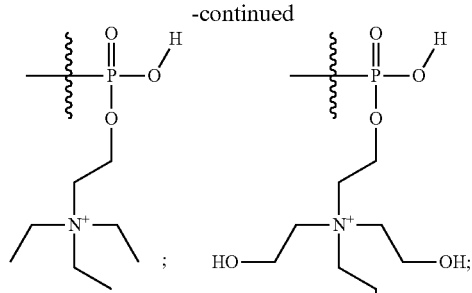
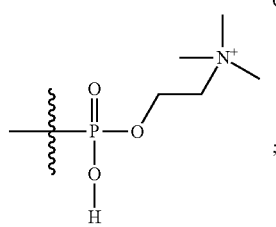
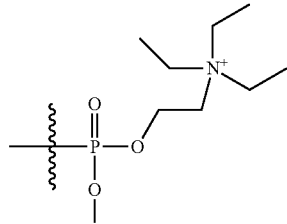
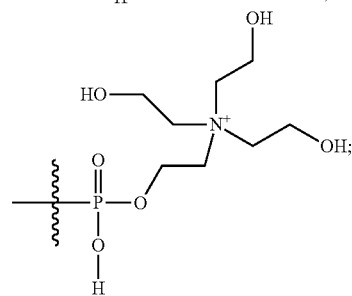
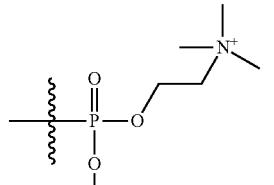
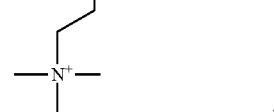
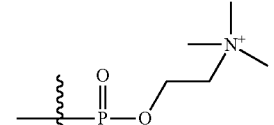
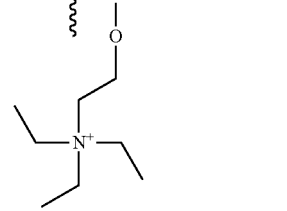
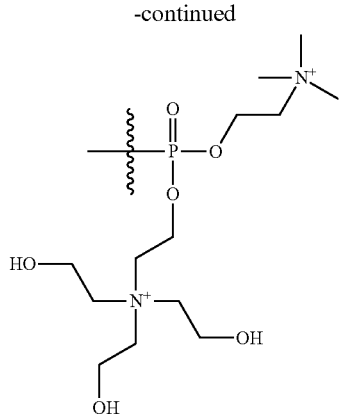
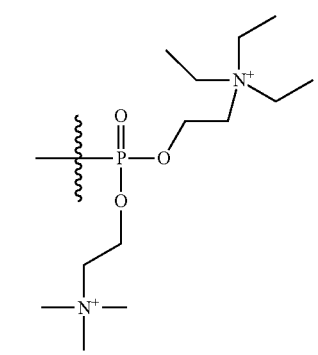
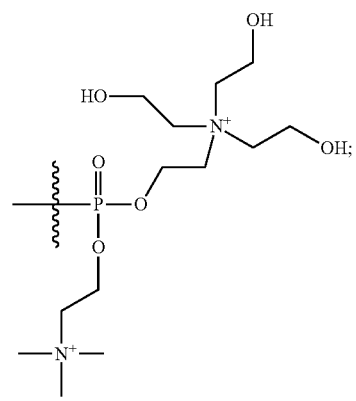
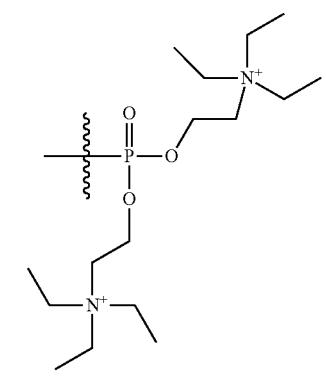

-continued

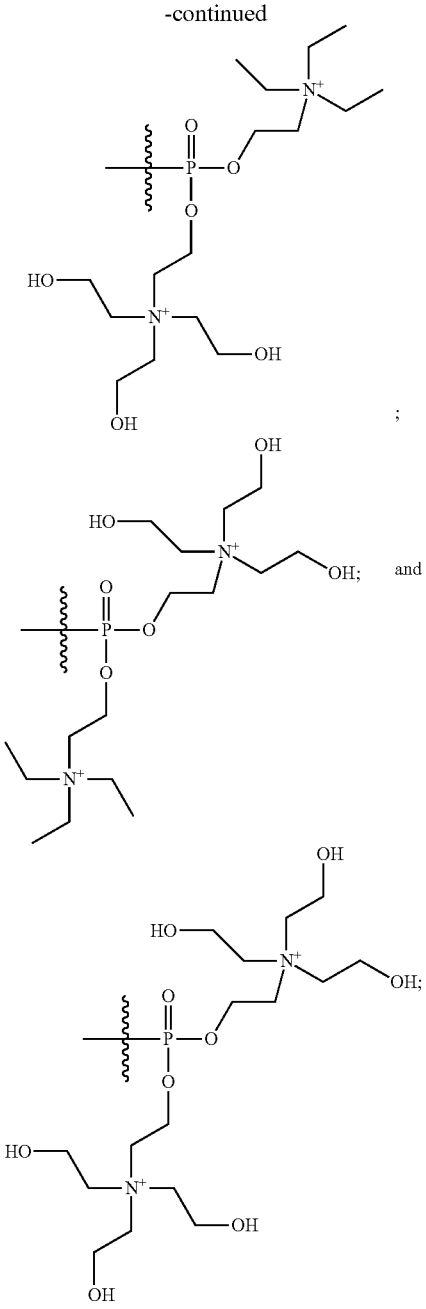

wherein aa is a naturally occurring amino acid side chain and n is an integer from 1 to 200; and a, b and c, are each independently 0, 1, 2, 3, 4, 5, or 6;
m and n are each independently 0, 1, 2, 3, or 4; and
p is 1, 2, 3, or 4.

2. The method of claim 1, wherein the modulating androgen receptor activity is for treating a condition or disease selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration.

3. The method of claim 2, wherein the condition or disease is prostate cancer.

4. The method of claim 3, wherein the condition or disease is androgen-dependent prostate cancer.

5. The method of claim 1, wherein $R^1$ and $R^2$ are each independently H, —CN, or halogen.

6. The method of claim 1, wherein $R^3$ and $R^4$ are each methyl.

7. The compound of claim 1, wherein at least one of $L^2$ and $L^3$ is substituted or unsubstituted group selected from a pyrrole, furan, thiophene, pyrazole, pyridine, pyridazine, pyrimidine, imidazole, thiazole, isoxazole, oxadiazole, thiadiazole, oxazole, triazole, isothiazole, triazine, tetrazine, oxazine, azepine, pyrrolidine, pyrroline, imidazoline, imidazolidine, pyrazoline, pyrazolidine, piperidine, dioxane, morpholine, dithiane, thiomorpholine, or piperazine.

8. The method of claim 1, wherein:

a) a is 0 or 1;

b) b is 0 or 1; or c) c is 0 or 1.

9. The method of claim 1, wherein the compound has one of the following structures (Ia), (Ib), (Ic) or (Id):

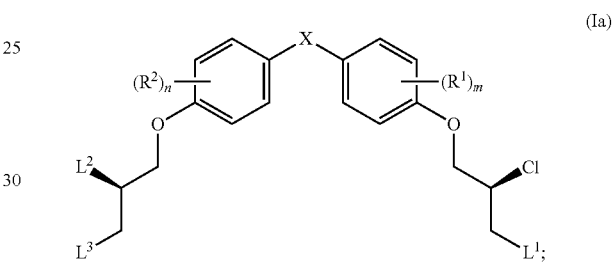

(Ia)

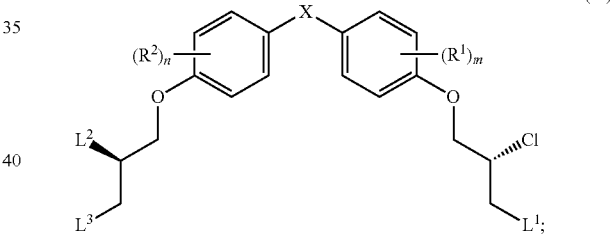

(Ib)

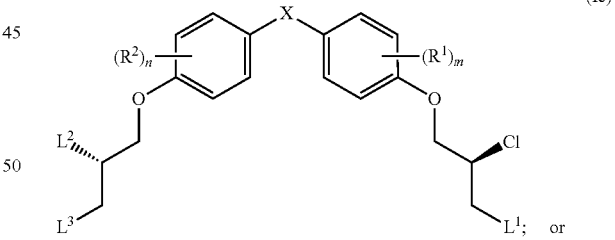

(Ic)

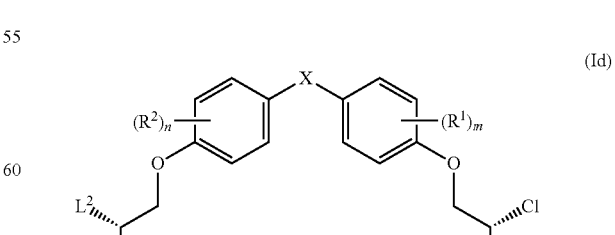

(Id)

10. The method of claim 1, wherein the compound is:
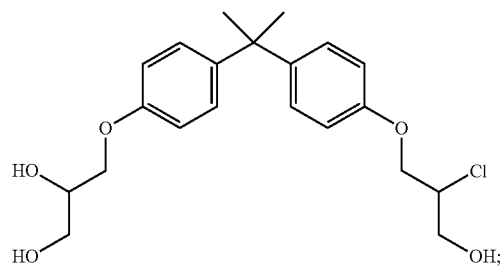
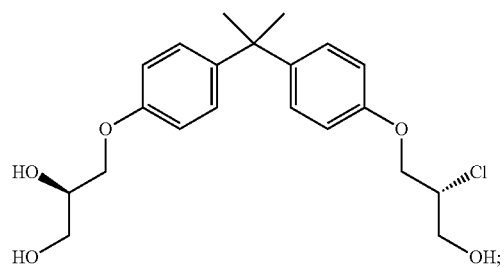
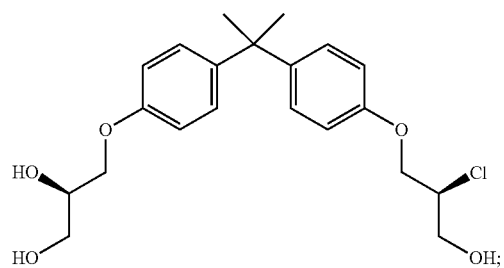
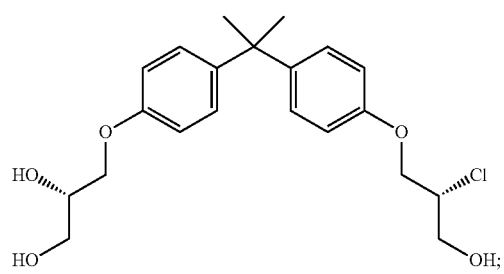
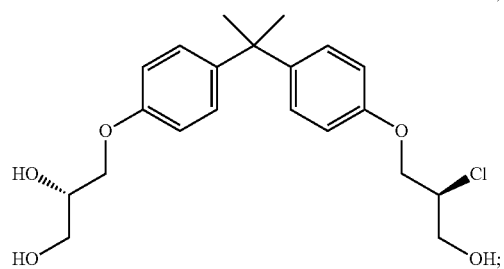
-continued
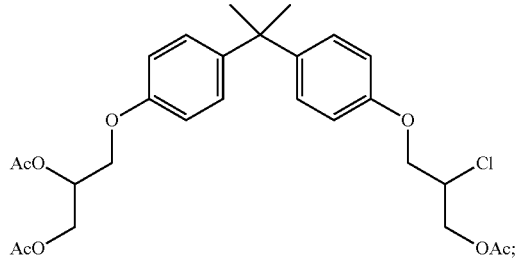
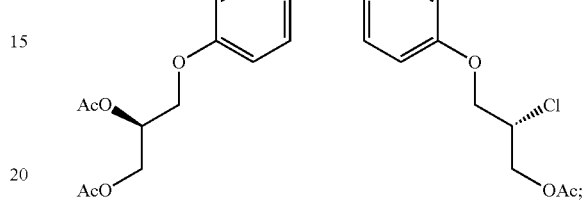
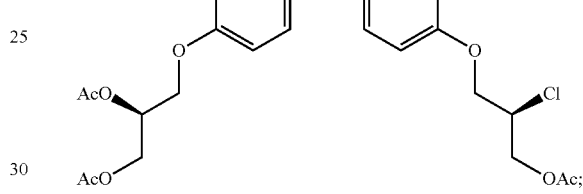
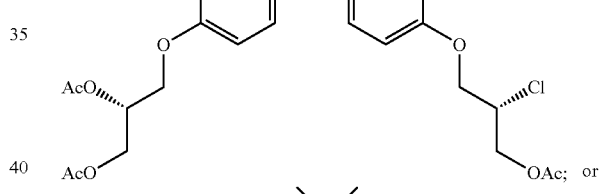
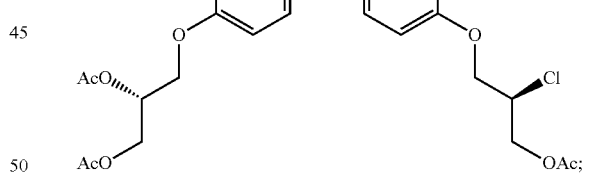 or
or a pharmaceutically acceptable salt, tautomer or stereoisomer thereof.
* * * * *